(12) United States Patent
Bothma et al.

(10) Patent No.: US 10,471,225 B2
(45) Date of Patent: Nov. 12, 2019

(54) IMPELLER AND MOTOR ASSEMBLY

(71) Applicant: Fisher & Paykel Healthcare Limited, Auckland (NZ)

(72) Inventors: Johannes Nicolaas Bothma, Otorohanga (NZ); Scott Bent, Auckland (NZ); Adam John Darby, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 664 days.

(21) Appl. No.: 14/652,687

(22) PCT Filed: Dec. 2, 2013

(86) PCT No.: PCT/IB2013/060549
§ 371 (c)(1),
(2) Date: Jun. 16, 2015

(87) PCT Pub. No.: WO2014/097030
PCT Pub. Date: Jun. 26, 2014

(65) Prior Publication Data
US 2015/0328418 A1  Nov. 19, 2015

Related U.S. Application Data

(60) Provisional application No. 61/738,910, filed on Dec. 18, 2012.

(51) Int. Cl.
*A61M 16/00* (2006.01)
*F04D 25/06* (2006.01)
(Continued)

(52) U.S. Cl.
CPC ..... *A61M 16/0066* (2013.01); *F04D 25/0606* (2013.01); *F04D 29/023* (2013.01);
(Continued)

(58) Field of Classification Search
CPC .......... A61M 16/0066; A61M 16/0069; A61M 16/16; A61M 2205/0216;
(Continued)

(56) References Cited

U.S. PATENT DOCUMENTS 2,929,944 A   3/1960  Shewmon
3,047,345 A   7/1962  Burton et al.
(Continued)

FOREIGN PATENT DOCUMENTS

CA   2636623 A1   7/2007
CN   1266150 A    9/2000
(Continued)

OTHER PUBLICATIONS

China First Office Action; 201280034511.4; dated Jul. 29, 2015; 28 pages.
(Continued)

*Primary Examiner* — Valerie L Woodward
(74) *Attorney, Agent, or Firm* — Knobbe, Martens, Olson & Bear, LLP

(57) ABSTRACT

A breathing assistance apparatus has a pressurised gases source featuring a lightweight impeller with a plastic shaft. The impeller is shroudless. The plastic shaft is supported within the stator by a bearing structure. A resilient motor mount couples the stator and the housing and provide compliance and/or damping for the motor.

20 Claims, 35 Drawing Sheets

(51) Int. Cl.
*F04D 29/02* (2006.01)
*F04D 29/053* (2006.01)
*F04D 29/28* (2006.01)
*A61M 16/16* (2006.01)
*A61M 16/10* (2006.01)

(52) U.S. Cl.
CPC ......... *F04D 29/053* (2013.01); *F04D 29/281* (2013.01); *A61M 16/0069* (2014.02); *A61M 16/109* (2014.02); *A61M 16/1095* (2014.02); *A61M 16/16* (2013.01); *A61M 2205/0216* (2013.01); *A61M 2205/0272* (2013.01); *A61M 2205/3368* (2013.01); *A61M 2205/362* (2013.01); *A61M 2205/3606* (2013.01); *A61M 2205/42* (2013.01); *A61M 2207/00* (2013.01); *F05D 2260/96* (2013.01); *F05D 2300/43* (2013.01)

(58) Field of Classification Search
CPC ... A61M 2205/0272; A61M 2205/3606; F04D 25/0606; F04D 29/281; F04D 29/26; F04D 29/263; H02K 1/28; H02K 1/30; H02K 7/00; H02K 310/51; H02K 1/06
See application file for complete search history.

(56) References Cited

U.S. PATENT DOCUMENTS

| | | | |
|---|---|---|---|
| 4,161,667 A | 7/1979 | Buckman | |
| 4,233,972 A | 11/1980 | Hauff et al. | |
| 4,357,552 A | 11/1982 | MacMillan | |
| 4,590,951 A | 5/1986 | O'Connor | |
| 4,623,812 A * | 11/1986 | van de Griend | H02K 1/30 310/216.124 |
| 5,211,171 A * | 5/1993 | Choromokos | A61M 1/0066 128/205.19 |
| 5,484,270 A * | 1/1996 | Adahan | A61M 16/20 128/205.13 |
| 5,567,127 A | 10/1996 | Wentz | |
| 5,608,591 A | 3/1997 | Klaassen | |
| 5,662,611 A * | 9/1997 | Beiser | A61B 1/00135 128/DIG. 13 |
| 5,797,727 A | 8/1998 | Peters et al. | |
| 5,875,783 A | 3/1999 | Draegerwerk | |
| 5,967,764 A | 10/1999 | Booth et al. | |
| 6,050,262 A | 4/2000 | Jay | |
| 6,073,630 A | 6/2000 | Adahan | |
| 6,376,952 B1 | 4/2002 | Stenta | |
| 6,439,861 B1 | 8/2002 | Shieh | |
| 6,487,047 B1 | 11/2002 | Balakrishnan | |
| 6,543,449 B1 | 4/2003 | Woodring et al. | |
| 6,622,724 B1 | 9/2003 | Truitt et al. | |
| 6,644,310 B1 | 11/2003 | Delache et al. | |
| 6,700,255 B1 | 3/2004 | Stenta | |
| 6,717,299 B2 | 4/2004 | Bacile et al. | |
| 6,722,359 B2 | 4/2004 | Chalvignac | |
| 6,802,648 B2 | 10/2004 | Merot et al. | |
| 6,910,483 B2 | 6/2005 | Daly et al. | |
| 7,121,874 B1 | 10/2006 | Jeon | |
| 7,244,099 B2 | 7/2007 | Yamasaki | |
| 7,384,237 B2 | 6/2008 | Baecke et al. | |
| 7,448,383 B2 | 11/2008 | Delache et al. | |
| 7,516,743 B2 | 4/2009 | Hoffman | |
| 7,913,692 B2 | 3/2011 | Kwok | |
| 8,011,362 B2 | 9/2011 | Adams | |
| 8,020,556 B2 | 9/2011 | Shahar | |
| 8,020,557 B2 | 9/2011 | Bordewick et al. | |
| 8,042,535 B2 | 10/2011 | Kenyon et al. | |
| 8,074,645 B2 | 12/2011 | Bordewick et al. | |
| 8,074,647 B2 | 12/2011 | Truitt et al. | |
| 8,080,907 B2 * | 12/2011 | Jeung | H02K 1/30 310/156.08 |
| 8,122,884 B2 | 2/2012 | Daly et al. | |
| 8,375,944 B2 | 2/2013 | Kwok | |
| D688,788 S | 8/2013 | Spruell et al. | |
| 8,553,364 B1 | 10/2013 | Schreiber et al. | |
| 8,638,014 B2 | 1/2014 | Sears et al. | |
| 8,973,576 B2 | 3/2015 | Kenyon | |
| 9,048,715 B2 * | 6/2015 | Kodani | H02K 1/2733 |
| 9,132,250 B2 | 9/2015 | Allum | |
| 9,132,252 B2 | 9/2015 | Barlow | |
| 10,137,264 B2 | 11/2018 | Darby et al. | |
| 2003/0235012 A1 | 12/2003 | Nishizawa | |
| 2005/0188989 A1 | 9/2005 | Delache et al. | |
| 2005/0202697 A1 | 9/2005 | Caveney et al. | |
| 2005/0210622 A1 | 9/2005 | Baecke et al. | |
| 2006/0017815 A1 | 1/2006 | Stavely et al. | |
| 2006/0096596 A1 | 5/2006 | Occhialini et al. | |
| 2006/0158785 A1 | 7/2006 | Arya et al. | |
| 2006/0237013 A1 | 10/2006 | Kwok | |
| 2007/0017518 A1 | 1/2007 | Farrugia et al. | |
| 2007/0132335 A1 * | 6/2007 | Ionel | H02K 1/22 310/261.1 |
| 2007/0251527 A1 | 11/2007 | Sleeper | |
| 2007/0277827 A1 | 12/2007 | Bordewick et al. | |
| 2007/0284952 A1 | 12/2007 | Ihle | |
| 2008/0149306 A1 | 6/2008 | Hwang et al. | |
| 2008/0178879 A1 | 7/2008 | Roberts et al. | |
| 2008/0216835 A1 | 9/2008 | McGinnis et al. | |
| 2008/0304986 A1 | 12/2008 | Kenyon et al. | |
| 2009/0071480 A1 | 3/2009 | Adams | |
| 2009/0194101 A1 | 8/2009 | Kenyon | |
| 2009/0301485 A1 | 12/2009 | Kenyon et al. | |
| 2009/0315492 A1 | 12/2009 | Oomura | |
| 2009/0320842 A1 | 12/2009 | Doherty | |
| 2009/0324435 A1 | 12/2009 | Sears et al. | |
| 2010/0059055 A1 | 3/2010 | Brungart et al. | |
| 2010/0059056 A1 | 3/2010 | Sears et al. | |
| 2010/0132711 A1 * | 6/2010 | Kenyon | A61M 16/0057 128/205.25 |
| 2010/0170513 A1 | 7/2010 | Bowditch et al. | |
| 2011/0023874 A1 | 2/2011 | Bath et al. | |
| 2011/0052205 A1 | 3/2011 | Yu et al. | |
| 2011/0073110 A1 | 3/2011 | Kenyon | |
| 2011/0132363 A1 | 6/2011 | Chalvignac | |
| 2012/0000463 A1 | 1/2012 | Bordewick et al. | |
| 2012/0080032 A1 | 4/2012 | Bordewick et al. | |
| 2012/0097156 A1 | 4/2012 | Bowman et al. | |
| 2012/0138058 A1 | 6/2012 | Fu et al. | |
| 2012/0152255 A1 | 6/2012 | Barlow et al. | |
| 2012/0167879 A1 | 7/2012 | Bowman | |
| 2012/0266873 A1 | 10/2012 | Lalonde | |
| 2012/0285454 A1 | 11/2012 | Nibu et al. | |
| 2013/0098359 A1 | 4/2013 | Becker et al. | |
| 2013/0152918 A1 | 6/2013 | Rummery | |
| 2013/0164158 A1 | 6/2013 | Matsuba et al. | |
| 2013/0306072 A1 | 11/2013 | Moir | |
| 2014/0020684 A1 | 1/2014 | Klasek et al. | |
| 2014/0069432 A1 * | 3/2014 | Mebasser | A61M 16/0066 128/205.25 |
| 2014/0178079 A1 | 6/2014 | Yagisawa et al. | |
| 2014/0216460 A1 | 8/2014 | Bothma et al. | |
| 2014/0227091 A1 | 8/2014 | Kenyon et al. | |
| 2014/0242816 A1 | 8/2014 | Rathburn | |
| 2015/0136140 A1 | 5/2015 | Kenyon et al. | |
| 2015/0136467 A1 | 5/2015 | Rathburn | |
| 2015/0157818 A1 | 6/2015 | Darby et al. | |
| 2015/0301567 A1 | 10/2015 | Chen et al. | |
| 2016/0010649 A1 | 1/2016 | Aiello | |
| 2016/0087505 A1 | 3/2016 | Turner et al. | |
| 2016/0192507 A1 | 6/2016 | Rathburn | |
| 2017/0204868 A1 | 7/2017 | Oshita et al. | |
| 2018/0156233 A1 | 6/2018 | Sawada et al. | |

FOREIGN PATENT DOCUMENTS

| | | |
|---|---|---|
| CN | 101296722 A | 10/2008 |
| CN | 101321958 A | 12/2008 |
| CN | 101449064 A | 6/2009 |
| CN | 101466429 A | 6/2009 |
| DE | 3310376 A1 | 9/1984 |
| EP | 1035330 B1 | 9/2000 |

(56) References Cited

FOREIGN PATENT DOCUMENTS

| | | |
|---|---|---|
| EP | 1205203 A2 | 5/2002 |
| EP | 1205203 A3 | 7/2002 |
| EP | 1205203 B1 | 9/2004 |
| EP | 1760319 A1 | 3/2007 |
| EP | 1205203 B1 | 3/2011 |
| EP | 2 317 150 A1 | 5/2011 |
| GB | 948382 A | 2/1964 |
| GB | 1041313 A | 9/1966 |
| JP | 2002-511786 A | 4/2002 |
| JP | 2004-353655 A | 12/2004 |
| JP | 2007-506482 A | 3/2007 |
| JP | 2009-533153 A | 9/2009 |
| JP | 2013-501541 A | 1/2013 |
| WO | WO 2007/048206 A1 | 5/2007 |
| WO | WO 2007/134405 A1 | 11/2007 |
| WO | WO 2008/028247 | 3/2008 |
| WO | WO 2008/092235 A1 | 8/2008 |
| WO | WO 2010/028121 | 3/2010 |
| WO | WO 2010/096467 A1 | 8/2010 |
| WO | WO 2011/017763 A1 | 2/2011 |
| WO | WO 2011/022779 A1 | 3/2011 |
| WO | WO 2011/062633 | 5/2011 |
| WO | WO 2011/112807 | 9/2011 |
| WO | WO 2012/024740 | 3/2012 |
| WO | WO 2012/094230 | 7/2012 |
| WO | WO 2012/113027 | 8/2012 |
| WO | WO 2012/145358 A2 | 10/2012 |
| WO | WO 2012/174602 | 12/2012 |
| WO | WO 2013/020167 | 2/2013 |
| WO | WO 2016/009771 A1 | 1/2016 |
| WO | WO 2016/194697 A1 | 12/2016 |
| WO | WO 2017/006189 A1 | 1/2017 |
| WO | WO 2017/068530 A3 | 4/2017 |

OTHER PUBLICATIONS

Japanese Examination Report with English Translation, dated Dec. 19, 2016; 8 pages.
International Search Report; PCT/NZ2012/000124; dated Oct. 29, 2012; 6 pages.
Written Opinion; PCT/NZ2012/000124; dated Oct. 29, 2012; 9 pages.
Sep. 24, 2013 International Search Report and Written Opinion for Application No. PCT/NZ2013/000006 filed Feb. 1, 2013.
Sep. 24, 2013 Written Opinion for Application No. PCT/NZ2013/000006 filed Feb. 1, 2013.
European Search Report for Application No. EP 17 15 7168, dated Jun. 12, 2017 in 7 pages.
China First Office Action; 201380018302.5; dated Nov. 4, 2015; 9 pages.
European Search Report; dated Jul. 20, 2015; 13 pages.
International Search Report; PCT/IB2013/060549; dated Mar. 19, 2014; 5 pages.
Written Opinion; PCT/IB2013/060549, dated Mar. 19, 2014; 6 pages.
Examination Report for Australian Application No. 2017204037, dated Nov. 16, 2017; 3 pages.
Examination Report No. 2 for Australian Application No. 2017204037, dated Jan. 3, 2018; 2 pages.
China First Office Action; Application No. 2018062302200570; dated Jul. 3, 2018; 5 pages
Examination Report for Australian Application No. 2013285620, dated Nov. 9, 2016; 3 pages.
European Communication; 13812942.4; dated Apr. 12, 2018; 5 pages.
International Search Report and Written Opinion of the International Searching Authority for International Application No. PCT/NZ2018/050056, dated Sep. 11, 2018, in 49 pages.
Australian Office Action; 2017261486; dated Jan. 23, 2019; 3 pages.
European Communication; 13812942.4; dated Nov. 11, 2018; 6 pages.
Canadian Office Action; 2912244; dated Nov. 5, 2018; 5 pages.
Australian Office Action; 2018200350; dated Dec. 17, 2018; 4 pages.

* cited by examiner

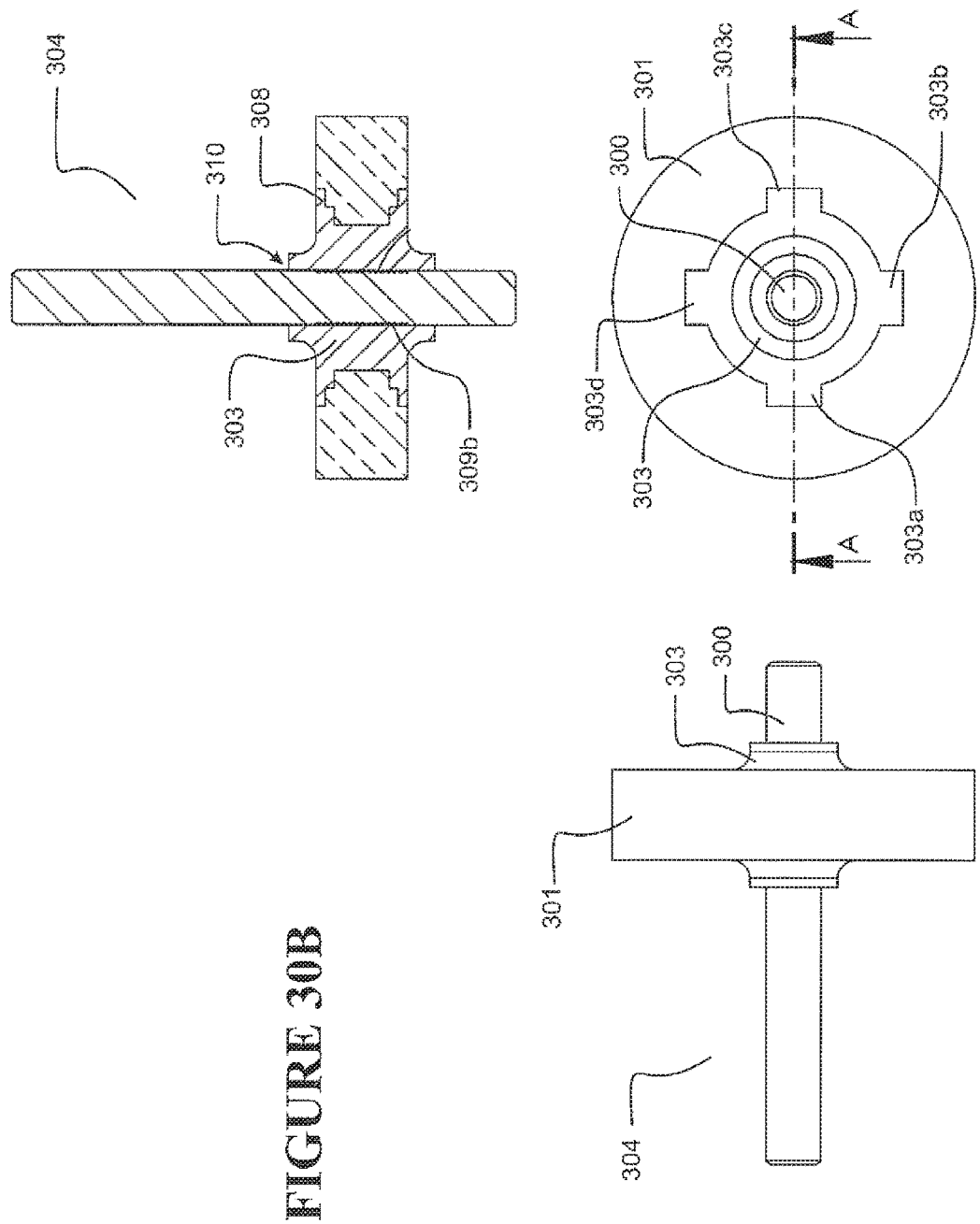

IMPELLER AND MOTOR ASSEMBLY

BACKGROUND OF THE INVENTION

Field of the Invention

This invention relates to a gases supply and gases humidification apparatus, particularly but not solely for providing respiratory assistance to patients or users who require a supply of gas for the treatment of diseases such as Obstructive Sleep Apnea (OSA), snoring, or Chronic Obstructive Pulmonary Disease (COPD) and the like. In particular, this invention relates to a compressor or blower for use in a gases supply apparatus which in use is integral with the gases supply apparatus.

Description of the Related Art

Devices or systems for providing a humidified gases flow to a patient for therapeutic purposes are well known in the art. Systems for providing therapy of this type, for example CPAP therapy, have a structure where gases at the required pressure are delivered from a blower (also known as a compressor, an assisted breathing unit, a fan unit, a flow generator or a pressure generator) to a humidifier chamber downstream from the blower. As the gases are passed through the heated, humidified air in the humidifier chamber, they become saturated with water vapour. The gases are then delivered to a user or patient downstream from the humidifier, via a gases conduit.

Humidified gases can be delivered to a user from a modular system that has been assembled from separate units (that is, a system where the humidifier chamber/heater and the breathing unit/blower are separate items) connected in series via conduits. A schematic view of a user 1 receiving air from a modular assisted breathing unit and humidifier system (together or separately a "breathing assistance apparatus") is shown in FIG. 1. Pressurised air is provided from an assisted breathing unit or blower 2a via a connector conduit 10 to a humidifier chamber 4a. Humidified, heated and pressurised gases exit the humidifier chamber 4a via a user conduit 3, and are provided to the patient or user 1 via a user interface 5.

It is becoming more common for integrated blower/humidifier systems to be used. A typical integrated system ("breathing assistance apparatus") consists of a main blower or assisted breathing unit which provides a pressurised gases flow, and a humidifier unit that mates with or is otherwise rigidly connected to the blower unit. This mating occurs for example by a slide-on or push connection, so that the humidifier is held firmly in place on the main blower unit. A schematic view of the user 1 receiving air from an integrated blower/humidifier unit 6 is shown in FIG. 2. The system operates in the same manner as the modular system shown in FIG. 1, except that humidifier chamber 4b has been integrated with the blower unit to form the integrated unit 6.

The user interface 5 shown in FIGS. 1 and 2 is a nasal mask, covering the nose of the user 1. However, it should be noted that in systems of these types, a mask that covers the mouth and nose, a full face mask, a nasal cannula, or any other suitable user interface could be substituted for the nasal mask shown. A mouth-only interface or oral mask could also be used. Also, the patient or user end of the conduit can be connected to a tracheostomy fitting, or an endotracheal intubation.

U.S. Pat. No. 7,111,624 includes a detailed description of an integrated system. A 'slide-on' water chamber is connected to a blower unit in use. A variation of this design is a slide-on or clip-on design where the chamber is enclosed inside a portion of the integrated unit in use. An example of this type of design is shown in WO 2004/112873, which describes a blower, or flow generator 50, and an associated humidifier 150.

For these systems, the most common mode of operation is as follows: air is drawn by the blower through an inlet into the casing which surrounds and encloses at least the blower portion of the system. The blower (controlled by a microcontroller, microprocessor or similar) pressurises the air stream from the flow generator outlet and passes this into the humidifier chamber. The air stream is heated and humidified in the humidifier chamber, and exits the humidifier chamber via an outlet. A flexible hose or conduit is connected either directly or indirectly to the humidifier outlet, and the heated, humidified gases are passed to a user via the conduit. This is shown schematically in FIG. 2.

Impeller type fans or blowers are most commonly used in breathing systems of this type. An impeller blade unit is contained within an impeller housing. The impeller blade unit is connected to a drive of some form by a central spindle. A typical impeller housing is shown in FIGS. 3 and 4. A typical rotating impeller unit 154, having a plurality of blades 151 and a shroud 152, which in use is located inside the housing is shown in FIGS. 5 and 6. Air is drawn into the centre of the impeller unit through an aperture, and is then forced outwards from the centre of the housing towards an exit passage (usually located to one side of the housing) by the blades of the rotating impeller unit.

Generally, domestic users receive treatment for sleep apnea or similar. It is most common for a nasal mask, or a mask that covers both the mouth and nose, to be used. If a nasal mask is used, it is common to strap or tape the mouth closed, so that the use of the system is effective (mouth leak and the associated pressure drop are substantially reduced or eliminated). For the range of flows dictated by the user's breathing, the CPAP device pressure generator provides a flow of gases at a substantially constant pressure. The pressure can usually be adjusted before use, or during use, either by a user, or a medical professional who sets up the system. Systems that provide variable pressure during use are also known—for example BiPAP machines that provide two levels of pressure: One for inhalation (IPAP) and a lower pressure during the exhalation phase (EPAP). Variable pressure or constant pressure systems are all "breathing assistance apparatus"

SUMMARY OF THE INVENTION

It is an object of the present invention to provide an improved impeller or blower/compressor for use with a breathing assistance apparatus or an improved breathing assistance apparatus.

In one aspect the present invention may be said to consist in a breathing assistance apparatus comprising: a pressurised gases source comprising: a gases inlet, a gases outlet adapted to emit pressurised gases to an outlet of the breathing assistance apparatus, and a lightweight impeller on a rotatable plastic shaft.

Preferably the lightweight impeller is shroudless or otherwise has reduced material.

Preferably the breathing assistance apparatus further comprises a motor with a stator, wherein the rotatable plastic shaft is located within the stator, and the motor further comprises at least one bearing structure to support the rotatable plastic shaft within the stator, the bearing structure having one or more bearing mounts.

Preferably the bearing mounts provide compliant support to the rotatable shaft.

Preferably the motor further comprises a rotor within the stator, the plastic shaft being formed and coupled to the rotor by injection moulding.

In another aspect the present invention may be said to consist in A breathing assistance apparatus comprising: a motor comprising a rotatable plastic shaft located within a stator, a bearing structure to support the rotatable shaft in the stator, the bearing structure having one or more bearing mounts.

Preferably the bearing mounts provide compliant support to the rotatable shaft.

Preferably the motor further comprises a rotor within the stator, the plastic shaft being formed and coupled to the rotor by injection moulding.

In another aspect the present invention may be said to consist in a breathing assistance apparatus comprising: a pressurised gases source comprising: a housing, a gases inlet, a gases outlet adapted to emit pressurised gases to an outlet of the breathing assistance apparatus, a motor with a rotatable plastic shaft and at least one bearing structure to support the rotatable shaft within a stator, the bearing structure having one or more flexible and/or resilient bearing mounts to provide compliance and/or preload and/or damping for the rotatable shaft, a lightweight impeller coupled to the rotatable plastic shaft, a flexible and/or resilient motor mount that couples the stator and the housing to provide compliance and/or damping for the motor, a partition to define first and second interior regions within the housing, wherein the first and second regions are fluidly connected by a crescent shaped opening formed in or by the partition.

Preferably the lightweight impeller is shroudless or otherwise has reduced material.

Preferably the motor further comprises a rotor within the stator, the plastic shaft being formed and coupled to the rotor by injection moulding.

In another aspect the present invention may be said to consist in a method of manufacturing a shaft and rotor assembly for a motor comprising: inserting a rotor with a central opening into a first mould part, supporting a shaft extended through the central opening, coupling a second mould part to the first mould part to create a mould cavity around the central opening, injection moulding a plastic insert between the plastic shaft and the central opening to couple the plastic shaft to the rotor.

In another aspect the present invention may be said to consist in a method of manufacturing a shaft and rotor assembly for a motor comprising: inserting a rotor with a central opening into a first mould part, coupling a second mould part to the first mould part to create a mould cavity around the central opening, injection moulding a plastic shaft that extends through and couples to the central opening of the rotor.

Preferably the motor comprises a plastic rotatable shaft extending through an opening in a magnet rotor and being coupled thereto.

Also described is a breathing assistance apparatus comprising: a pressurised gases source comprising: a gases inlet, a gases outlet adapted to emit pressurised gases to an outlet of the breathing assistance apparatus, and a lightweight impeller.

Preferably lightweight impeller is shroudless or otherwise has reduced material.

Preferably lightweight impeller is formed in one piece.

Preferably the lightweight impeller has a radius of between 15 and 60 mm.

Preferably the lightweight impeller has a mass of less than 2 grams and preferably between 0.8 and 1.8 grams.

Preferably the lightweight impeller has a pressure to inertia to radius ratio greater than 50:1 Pa per gram*mm, and preferably greater than 80:1 Pa per gram*mm.

Preferably the lightweight impeller has a moment of inertia to radius ratio less than 15 g*mm and preferably within the range of 8 to 12 g*mm.

Preferably the lightweight impeller has a blade sweep volume to a blade volume ratio of 16:1 or greater.

Preferably the impeller is a centrifugal impeller rotatable about a central axis.

Preferably the breathing assistance apparatus comprises a motor for driving the impeller wherein the motor is operated using field oriented control.

Preferably the gases source further comprises a housing having upper and lower internal surfaces that enclose the impeller, and wherein the impeller has a plurality of blades that are substantially open to the upper and lower internal surfaces of the housing by virtue of being shroudless.

Preferably the housing forms part of or is integrated with the breathing assistance apparatus.

Preferably the gases source further comprises a partition to define first and second interior regions within the housing, wherein the first and second regions are fluidly connected by an opening formed in or by the partition.

Preferably the opening formed in or by the partition is at least partially circumferential.

Preferably opening formed in or by the partition is crescent shaped.

Preferably the first region is defined by the housing and the partition and comprises the gases inlet.

Preferably the second region is defined by the housing and the partition and comprises the gases outlet.

Preferably the impeller has an axis of rotation, the partition extending radially from the axis of rotation.

Preferably the housing further comprises a volute in the second region.

Preferably the opening is proximate the periphery of the volute.

Preferably the impeller is located within the first region.

Preferably a distal end of the impeller blades curve in the direction of blade rotation.

Preferably the breathing assistance apparatus further comprises a motor, the motor comprising: a rotatable shaft located within a stator, and at least one bearing structure to support the rotatable shaft within the stator, the bearing structure having one or more bearing mounts.

Preferably the bearing mount provides compliant support to the rotatable shaft.

Preferably an outer portion of the one or more bearing mounts engages the stator and/or a stator frame and/or other structure.

Preferably an outer portion of the one or more bearing mounts engages the stator and/or frame of the stator.

Preferably the stator comprises a stator frame, an inner surface of the stator frame engages with the bearing structure.

Preferably the bearing structure further comprises one or more bearings supported by the bearing mounts about the axis of the rotatable shaft.

Preferably the pressurised gases source has a housing and the breathing apparatus further comprises a motor mount that couples the stator and the housing to provide compliant support to the motor.

Preferably the bearing mount and/or motor mount are flexible and/or resilient.

Preferably the volute has a tongue at least partially defining a transition between the volute and the gases outlet, the tongue located in the second interior region.

Preferably the bearing mounts have a curved annular body and when engaged with the stator and/or stator frame and/or other structure the annular body is coerced into an engaged configuration that provides preload to the one or more bearings.

Preferably the bearing mount is made from a material that provides resilience and/or flexibility to provide preload when in the engaged configuration.

Preferably the bearing mounts are made from a material that provides damping.

Preferably the motor is operated using field oriented control.

Also described is a breath assistance apparatus comprising: a motor comprising a rotatable shaft located within a stator, a bearing structure to support the rotatable shaft in the stator, the bearing structure having one or more bearing mounts.

Preferably the bearing mounts provide compliant support to the rotatable shaft.

Preferably an outer portion of the one or more bearing mounts engages the stator and/or a stator frame and/or other structure.

Preferably the stator comprises a stator frame, an inner surface of the stator frame engaging with the bearing structure.

Preferably the bearing structure further comprises one or more bearings supported by the bearing mounts about the axis of the rotatable shaft.

Preferably the bearing mount is flexible and/or resilient.

Preferably the bearing mounts have a curved annular body and when engaged with the stator and/or stator frame and/or other structure the annular body is coerced into an engaged configuration that provides preload to the one or more bearings.

Preferably the bearing mount is made from a material that provides resilience and/or flexibility to provide preload when in the engaged configuration.

Preferably the bearing mounts are made from a material that provides damping.

Also described is a pressurised gases source comprising: a centrifugal impeller driven by a motor within a housing, the housing having a gases inlet, a gases outlet and a partition to define first and second interior regions wherein the first and second regions are fluidly connected by an opening in the partition.

Preferably the first region is defined by the housing and the partition and comprises the gases inlet.

Preferably the second region is defined by the housing and the partition and comprises the gases outlet.

A pressurised gases source according to any of the above used in a breathing assistance apparatus according to any of the above.

Also described is a breathing assistance apparatus comprising: a pressurised gases source comprising: a housing a gases inlet, a gases outlet adapted to emit pressurised gases to an outlet of the breathing assistance apparatus, a motor with a rotatable shaft and at least one bearing structure to support the rotatable shaft within a stator, the bearing structure having one or more flexible and/or resilient bearing mounts to provide compliance and/or preload and/or damping for the rotatable shaft, a lightweight impeller coupled to the rotatable shaft, a flexible and/or resilient motor mount that couples the stator and the housing to provide compliance and/or damping for the motor a partition to define first and second interior regions within the housing, wherein the first and second regions are fluidly connected by a crescent shaped opening formed in or by the partition.

Preferably the lightweight impeller is shroudless or otherwise has reduced material.

Preferably the lightweight impeller is formed in one piece.

Preferably the lightweight impeller has a radius of between 15 and 60 mm.

Preferably the lightweight impeller has a mass of less than 2 grams and preferably between 0.8 and 1.8 grams.

Preferably the lightweight impeller has a pressure to inertia to radius ratio greater than 50:1 Pa per gram*mm, and preferably greater than 80:1 Pa per gram*mm.

Preferably the lightweight impeller has a moment of inertia to radius ratio less than 15 g*mm and preferably within the range of 8 to 12 g*mm.

Preferably the lightweight impeller has a blade sweep volume to a blade volume ratio of 16:1 or greater.

Also described is a pressurised gases source comprising: a gases inlet, a gases outlet, a motor with a shaft, and a lightweight impeller connected to the motor and rotatable to draw gases from the inlet and emit gases through the outlet, wherein the impeller is shroudless or otherwise has reduced material.

Preferably the impeller is a centrifugal impeller rotatable about a central axis.

Preferably the gases source further comprises a housing having upper and lower internal surfaces that enclose the impeller, and wherein the impeller has a plurality of blades that are substantially open to the upper and lower internal surfaces of the housing by virtue of being shroudless.

Preferably the housing forms part of or is integrated with a CPAP machine.

Preferably the gases source further comprises a partition to define first and second interior regions within the housing, wherein the first and second regions are fluidly connected by an opening formed in or by the partition.

Preferably the opening formed in or by the partition is at least partially circumferential.

Preferably the first interior region is defined by the housing and the partition and comprises the gases inlet.

Preferably the second interior region is defined by the housing and the partition and comprises the gases outlet.

Preferably the impeller has an axis of rotation, the partition extending radially from the axis of rotation.

Preferably the housing further comprises a volute in the second region.

Preferably the opening is proximate the periphery of the volute.

Preferably the impeller is located within the first region.

Preferably a distal end of the impeller blades curve in the direction of blade rotation.

Preferably the further comprising a motor, the motor comprising: a rotatable shaft located within a stator, and at least one bearing structure to support the rotatable shaft, the bearing structure having one or more bearing mounts engaged and axially aligned with the stator to provide compliant support to the rotatable shaft.

Preferably an outer portion of the one or more bearing mounts engages the stator.

Preferably the stator comprises a stator frame, an inner surface of the stator frame engaging with the bearing structure.

Preferably the bearing structure further comprises one or more bearings supported by the bearing mounts about the axis of the rotatable shaft.

Preferably the pressurised gases source further comprises a motor mount that couples the stator frame and the housing to provide compliant support to the motor.

Preferably the bearing mount is flexible and/or resilient.

Preferably the volute has a tongue at least partially defining a transition between the volute and the gases outlet, the tongue located in the second interior region.

Preferably the motor is vector controlled.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7).

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting. Where specific integers are mentioned herein which have known equivalents in the art to which this invention relates, such known equivalents are deemed to be incorporated herein as if individually set forth. The invention consists in the foregoing and also envisages constructions of which the following gives examples only.

BRIEF DESCRIPTION OF THE DRAWINGS

A preferred form of the present invention will now be described with reference to the accompanying drawings.

FIGS. 30A, 30B show a metal shaft and magnet rotor assembly forming part of a motor.

DETAILED DESCRIPTION OF THE PREFERRED EMBODIMENT

The present invention will be described with reference to a breathing assistance apparatus/system where the humidifier chamber is integrated with the gases supply unit (also referred to as a respirator unit or blower unit). However, it should be noted that the system is equally applicable to a modular system.

The present invention relates to a lightweight/low inertia impeller. The lightweight nature of the impeller provides low inertia.

Figure 7:
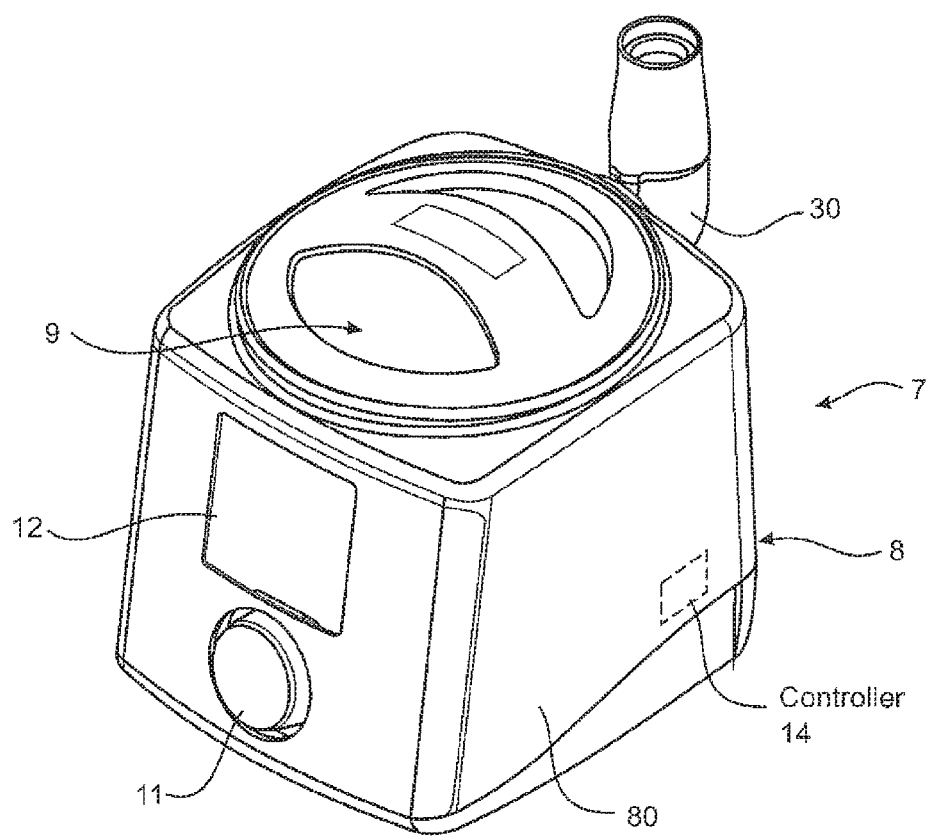
FIG. 7 shows a profiled view of a gases supply unit.

An example of an integrated gases supply unit 7 with which embodies the present invention is shown in FIG. 7—this is one example and should not be limiting. The integrated unit 7 comprises two main parts: a gases supply unit or blower unit 8 and a humidifier unit 9. Humidification unit 9 is partially enclosed within the external shell 80 of the blower unit 8 in use, except for the top of the humidification unit 9. It also comprises an internal controller 14 such as a microcontroller, microprocessor or similar for controlling the blower unit and other operations, such as that shown schematically in dotted lines. It is not necessary to describe the structure and operation of the humidification unit 9 in detail in order to fully describe the present invention.

The body of the gases supply unit 8 has the form of a generally rectangular block with substantially vertical side and rear walls, and a front face that is angled slightly rearwards (all the walls can be angled inwards slightly if required). In the preferred embodiment, the walls, base and top surface are all manufactured and connected as far as possible to minimise the occurrence of seams, and any necessary seams are sealed. As shown in FIG. 7, the gases supply unit 8 includes a control knob 11, located on the lower section of the front face of the gases supply unit 8, with a control display 12 located directly above the knob 11. A patient outlet 30 is shown passing out of the rear wall of the gases supply unit 8. In the preferred embodiment, the free end of the outlet 30 faces upwards for ease of connection. The patient outlet 30 is adapted to allow both pneumatic and electrical connection to one end of a conduit—e.g. conduit 3—running between the integrated unit 7 and a patient interface—e.g. interface 5. An example of the type of connector that can be used and the type of dual connection that can be made is described in U.S. Pat. No. 6,953,354. It should be noted that for the purposes of reading this specification, the patient interface can be thought of as including both the interface 5 and the conduit 3 where it would be appropriate to read it in this manner.

Figure 8:
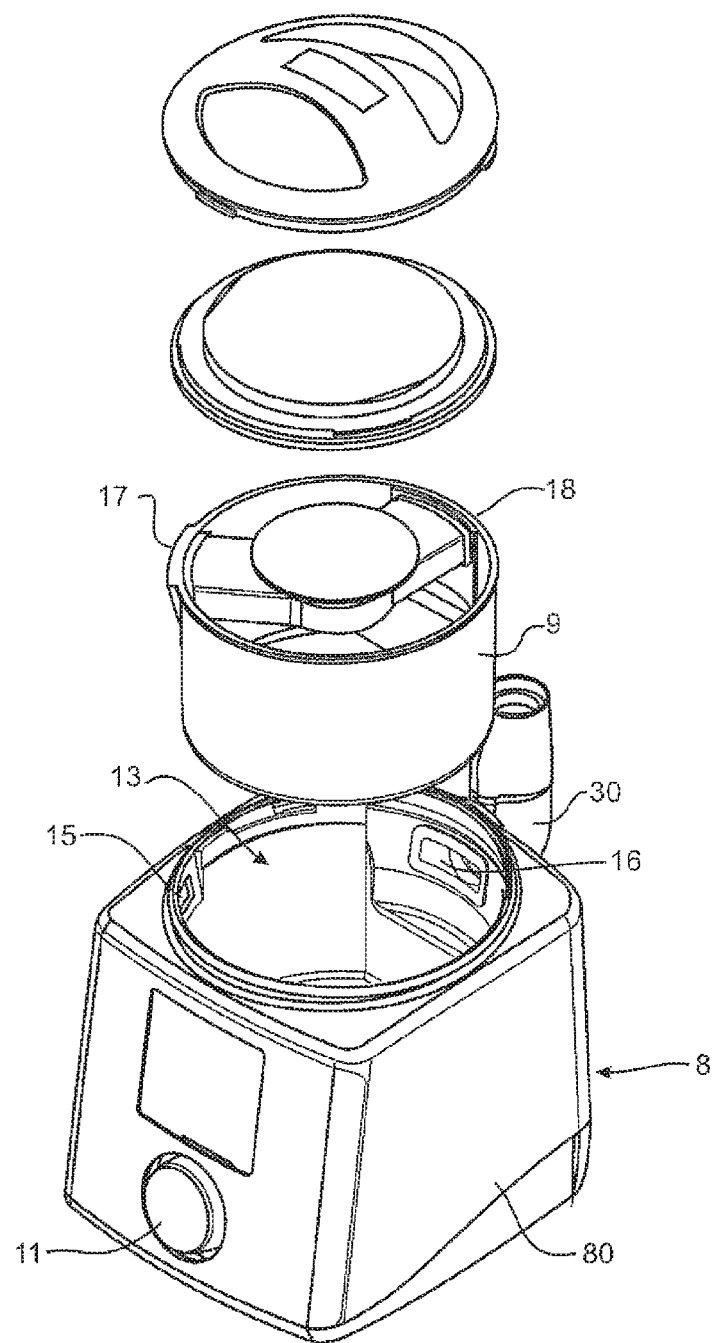
FIG. 8 shows an exploded view of the gases supply unit of FIG. 7.
Figure 9:
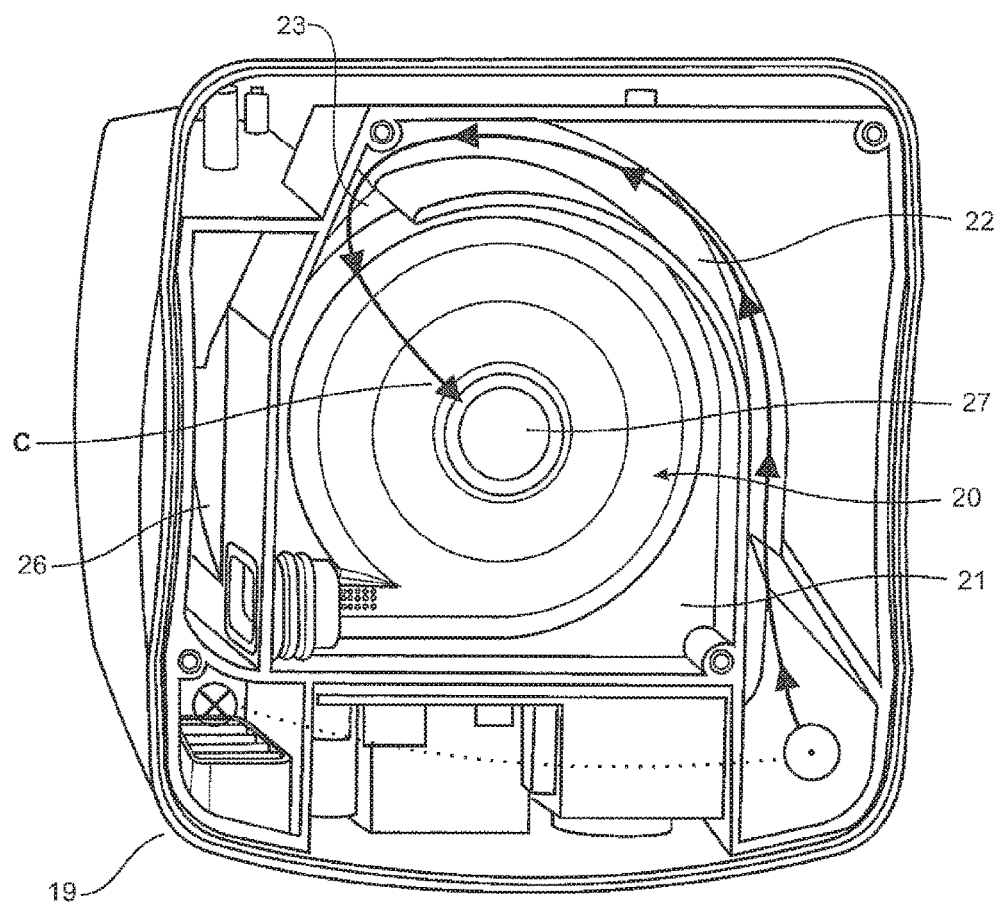
FIG. 9 shows an internal view of a gases supply unit (viewed from underneath).
Figure 10:
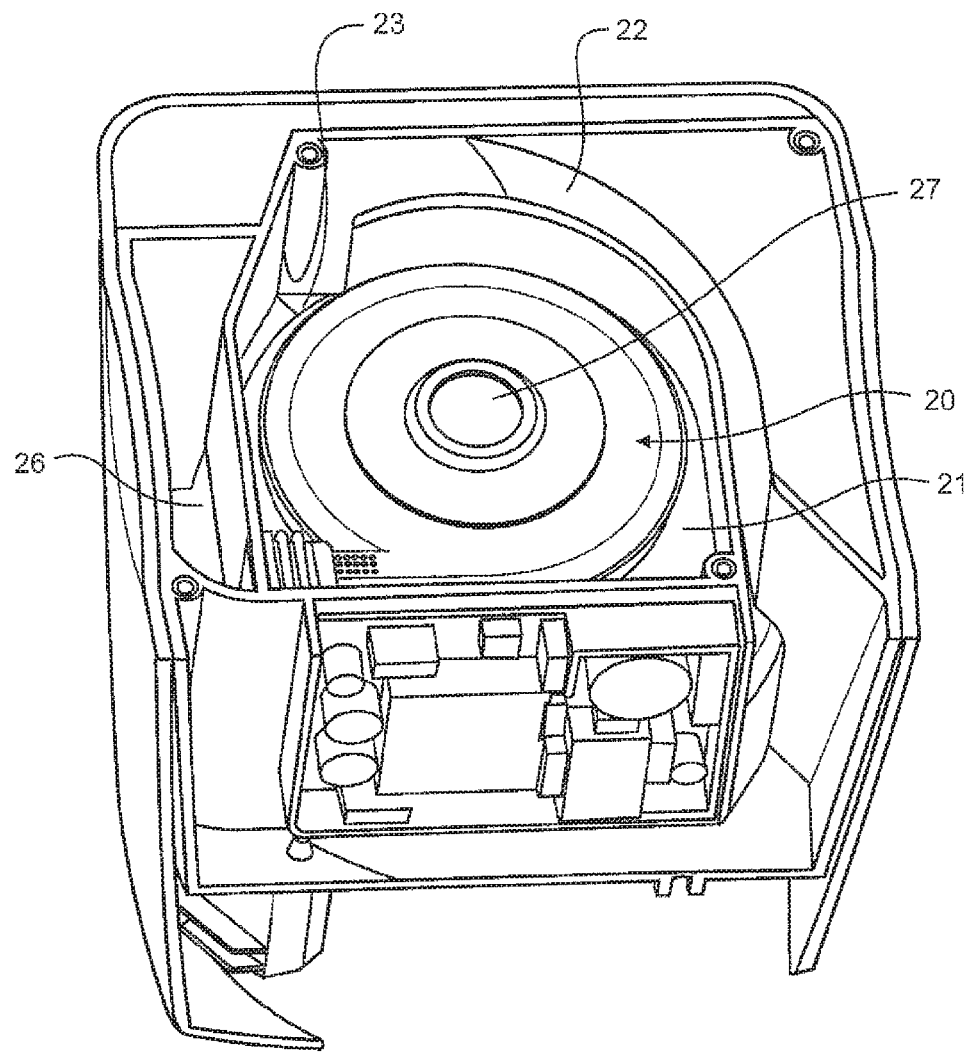
FIG. 10 shows a profiled view of the gases supply unit of FIG. 9.

The internal structure and components of the gases supply unit 8 will now be described with reference to FIGS. 8, 9 and 10. The gases supply unit 8 includes an enclosing external shell 80 which forms part of, and encloses, the gases supply unit 8. The shell 80 includes internal air passages for ducting air passing through the gases supply unit 8, and also internal recesses, cavities or slots into which components of the gases supply unit 8 is located in use. The shell 80 of the gases supply unit 8 is further adapted to include an open-topped compartment 13. In use, humidifier chamber 9 is located within the compartment 13. Blower unit 8 includes a heater base or heater plate, located at the bottom of the compartment 13. A humidifier inlet aperture 15 and humidifier outlet aperture 16 are located on the wall of the compartment 13, towards the top of the compartment 13. In the preferred embodiment, the inlet and outlet apertures 15, 16 are aligned so as to mate with inlet and outlet humidifier ports 17, 18 located on the humidifier chamber 9, when the system is in use. It should be noted that other forms of humidifier inlet are possible. For example, a conduit running between the gases supply unit 8 and e.g. the lid of the humidifier chamber 9. Also, if the humidifier chamber is a separate item (that is, not rigidly connected to the gases supply unit in use), the humidifier inlet aperture 15 will not be connected directly to the humidifier chamber, but will be connected instead to one end of a conduit or similar leading from the humidifier inlet aperture on the gases supply unit, to the humidifier chamber.

Air from atmosphere is drawn into the shell of the gases supply unit 8 through an atmospheric inlet vent 19. This vent 19 can be located wherever is convenient on the external surface of the shell of the gases supply unit 8. In the preferred embodiment, as shown in FIG. 9 (viewing the housing from underneath), the inlet vent 19 is located on the rear face of the shell of the gases supply unit 8, on the right hand side of the rear face (right hand side when looking forwards). In the preferred embodiment, air is drawn in through the inlet vent 19 by means of a fan unit 20 which forms part of the gases supply unit 8, and which is located inside the enclosing external shell of the gases supply unit 8. The fan unit 20 provides a pressurised gases stream for the gases supply unit and therefore the assisted breathing system. The fan unit 20 will be described in more detail below. The air is drawn into the fan unit 20 indirectly, via a curved inlet path 22 formed through the shell of the gases supply unit 8. Path C runs from the inlet vent 19 up over the power supply cavity and though the venturi (shown in dotted lines) past into curved path 22 (including absorber foam channel and through a thermistor flow sensor) to an aperture 23 formed in the gases supply unit shell 80, the aperture 23 passing into a recess/plenum 21 which is formed in the gases supply unit shell 80, in which the fan unit 20 is located. The air then passes into the inlet 27.

The gases stream passes through the fan unit 20 to the humidifier inlet aperture 15 as follows: the shell of the gases supply unit 8 includes a chamber or outlet duct 26 which forms at least part of an outlet air path to allow gaseous communication between the fan unit 20 and the humidifier inlet aperture 15. In the preferred embodiment, the outlet duct 26 runs up between the right hand side wall of the gases supply unit 8 (from behind looking forwards) and the front wall, up to the humidifier inlet aperture 15. As shown in FIGS. 9 and 10, air exiting the fan unit 20 enters the duct 26.

In use, air exits the shell of the gases supply unit or blower 8 via the humidifier inlet aperture 15 and enters the humidifier chamber 9. In the preferred form, the humidifier inlet aperture 15 forms an outlet at the end of the duct 26. The gases are humidified and heated in the chamber 9, before passing out of the chamber 9 through the humidifier outlet aperture 16, which is directly or indirectly connected to the patient outlet 30 (it should be noted that the outlet of the humidifier chamber 9 could also be completely separate from the gases supply unit 8). The heated humidified gas is then passed to the user 1 via conduit 3. The patient outlet 30 is adapted to enable pneumatic attachment of the patient conduit 3, and in the preferred embodiment, outlet 30 is also adapted to enable electrical connection via an electrical connector. A combined electrical and pneumatic connection can be useful for example if the conduit 3 is to be heated. Electrical heating of a conduit such as conduit 3 can prevent or minimise the occurrence of condensation within the conduit 3. It should also be noted that the outlet connection does not have to be via the shell of the integrated unit 7. If required, the connection for the conduit 3 could be located directly on an outlet from humidifier chamber 9.

The blower unit 8 in use is set to a user-specified pressure level and/or the pressure level can be automatically controlled. The flow rate for the preferred embodiment will vary during use, depending on the users breathing. The power to fan unit 20 can be altered, to change the speed at which the impeller 24 is rotating, and therefore the pressure.

The structure of the fan unit 20 according to one embodiment shall now be described, with particular reference to FIGS. 11, 12 and 13. The fan unit 20 is located in recess 21 of the shell of the gases supply unit 8 in use, as described above with reference to FIGS. 9 and 10. In the preferred form, the fan unit 20 comprises a rotating impeller located inside a casing having the form of a snail or scroll casing 25.

Figure 11:
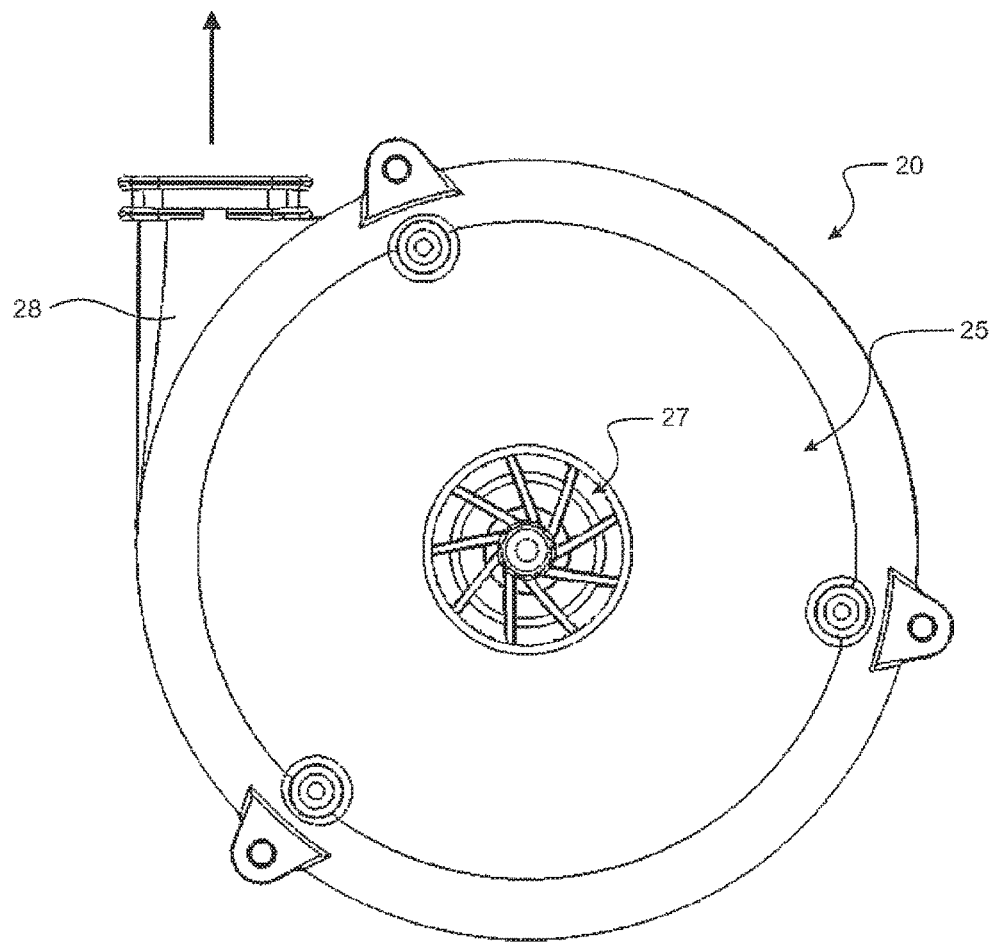
FIG. 11 shows a plan view of the top side of a blower unit of one embodiment.
Figure 12:
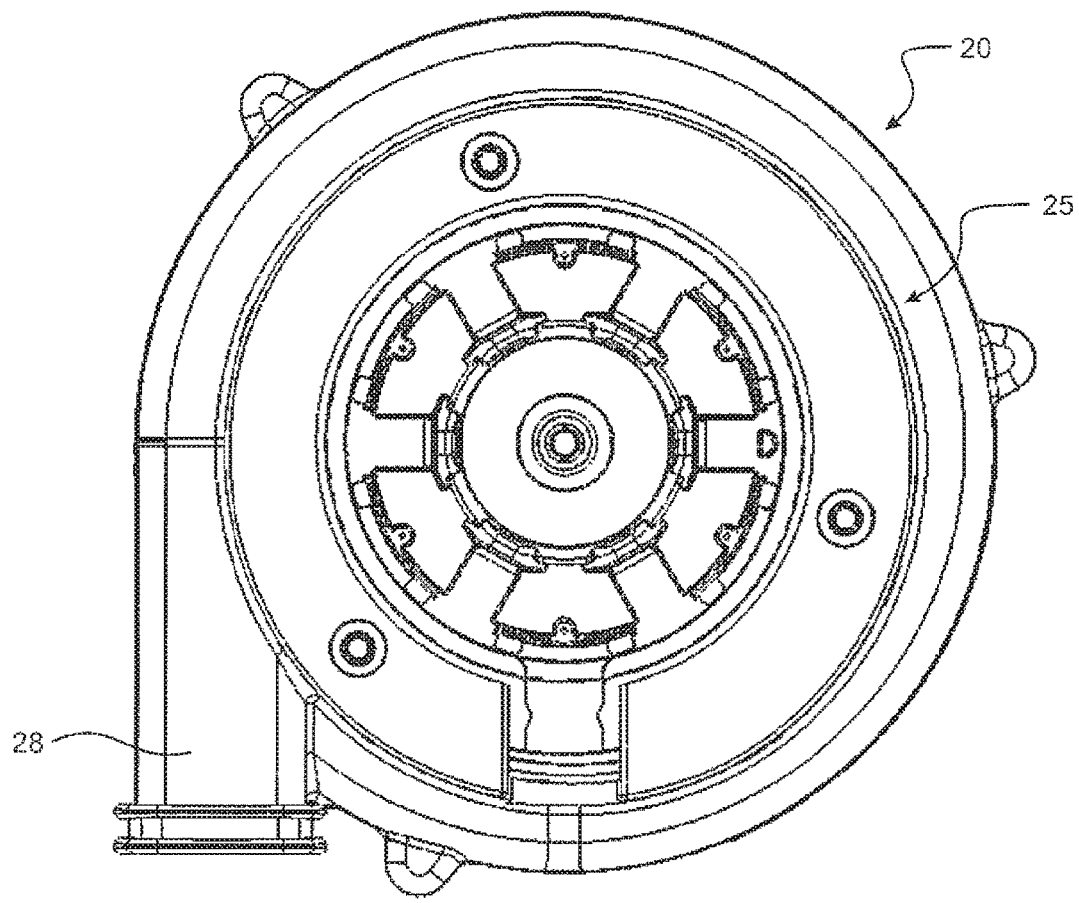
FIG. 12 shows a plan view of the bottom side of the blower unit of FIG. 11.
Figure 13:
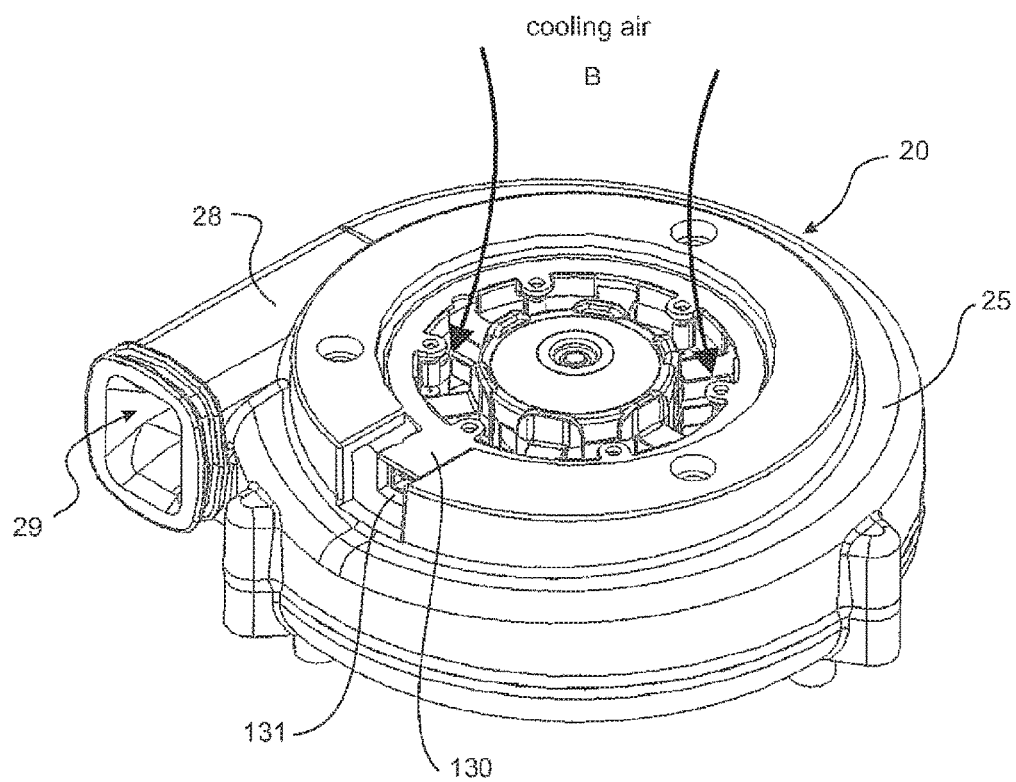
FIG. 13 shows a profile view of the bottom side of the blower unit of FIG. 12

It can be seen that the fan unit 20 appears generally circular in plan view, as shown in FIGS. 11 and 12. The fan casing 25 includes an inlet aperture 27. In the preferred form, inlet aperture 27 is a circular hole located in approximately the centre of the casing 25 and passing from the outside of the casing to the inside. Air from the inlet path 22 (see FIG. 10) enters the fan casing 25 via the inlet aperture 27. It should be noted that where it would be appropriate to include the aperture 23 and at least part of the recess 21 as part of the air inlet path, the specification should be read as including these elements. The preferred form of the casing 25 of the fan unit 20 also includes an outlet passage 28.

In the preferred form, the outlet passage 28 is a short passage formed as an integral part of the casing 25 and aligned substantially tangentially to the circumference to the remainder of the generally circular casing 25. A fan casing outlet aperture or exit aperture 29 (see e.g. FIG. 13) is located at the outer end of the passage 28. It should be noted that the fan casing exit aperture 29 could be located wherever is convenient on the passage 28 (i.e. it does not have to be at the end of the passage, it could be through the passage wall partway along its length, for example). Exit aperture 29 opens into the duct 26. The outlet passage 28 forms part of the air path from the fan to the humidifier inlet aperture 15.

The fan casing 25 encloses the fan in use, except for the inlet aperture 27 and the exit aperture 29 of the passage 28. In the preferred embodiment, rotation of the fan unit 20 is driven by a motor, the fan or impeller unit being adapted for connection to the motor. Air or gases are drawn through inlet aperture 27 in the centre of the casing 25, into the centre of the impeller unit 24, and are then forced outwards as a gases stream through the exit aperture 29 of the outlet passage 28 by the impeller blades 31 as the impeller unit 24 rotates.

In the preferred form, the fan outlet passage or exit passage 28 has a generally rectangular cross-section, and the exit passage 28 is aligned substantially tangentially to the casing 25. However, the cross-section of the fan outlet passage 28 could be any suitable shape, such as oval, rectangular or circular. The fan outlet passage 28 could also be arranged at any suitable angle to the impeller unit, for example facing radially outwards, or at any suitable angle between tangential and radial. The fan outlet passage 28 causes the gases forced outwards by the impeller unit 24 to coalesce as a fluidic gases stream, and dictates the direction in which the gases stream flows. The overall path or overall direction of the gases flow will be along the passage from the fan towards the fan casing exit aperture 29.

Figure 1:
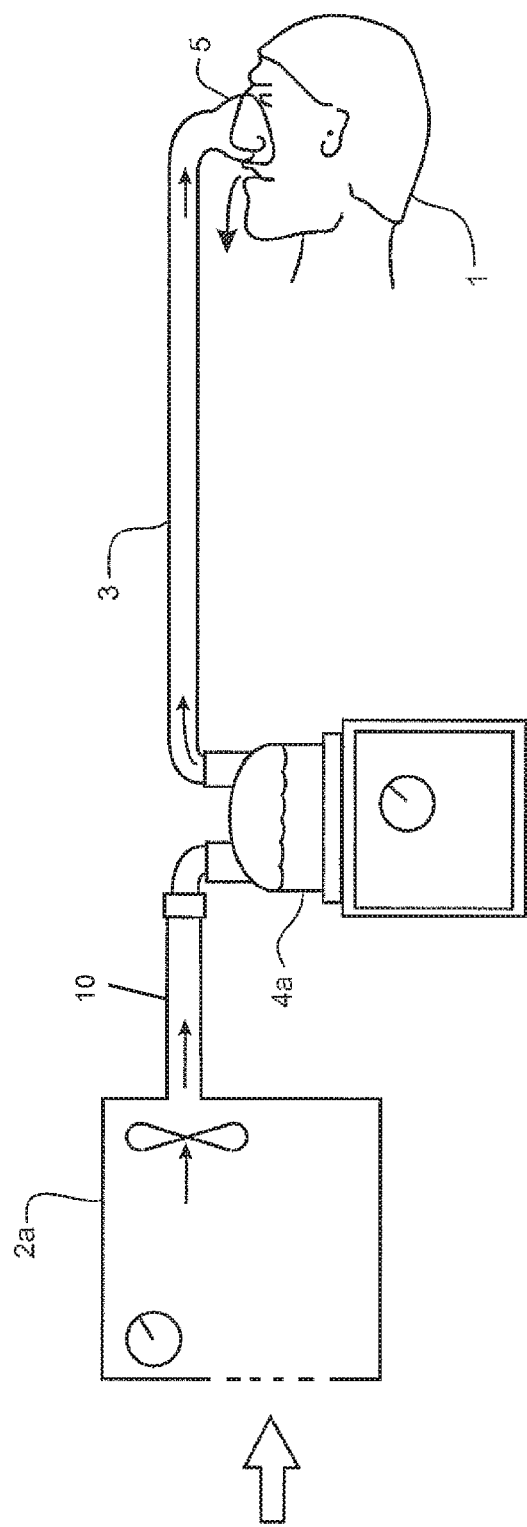
FIG. 1 shows a schematic view of a modular assisted breathing unit and humidifier system.
Figure 2:
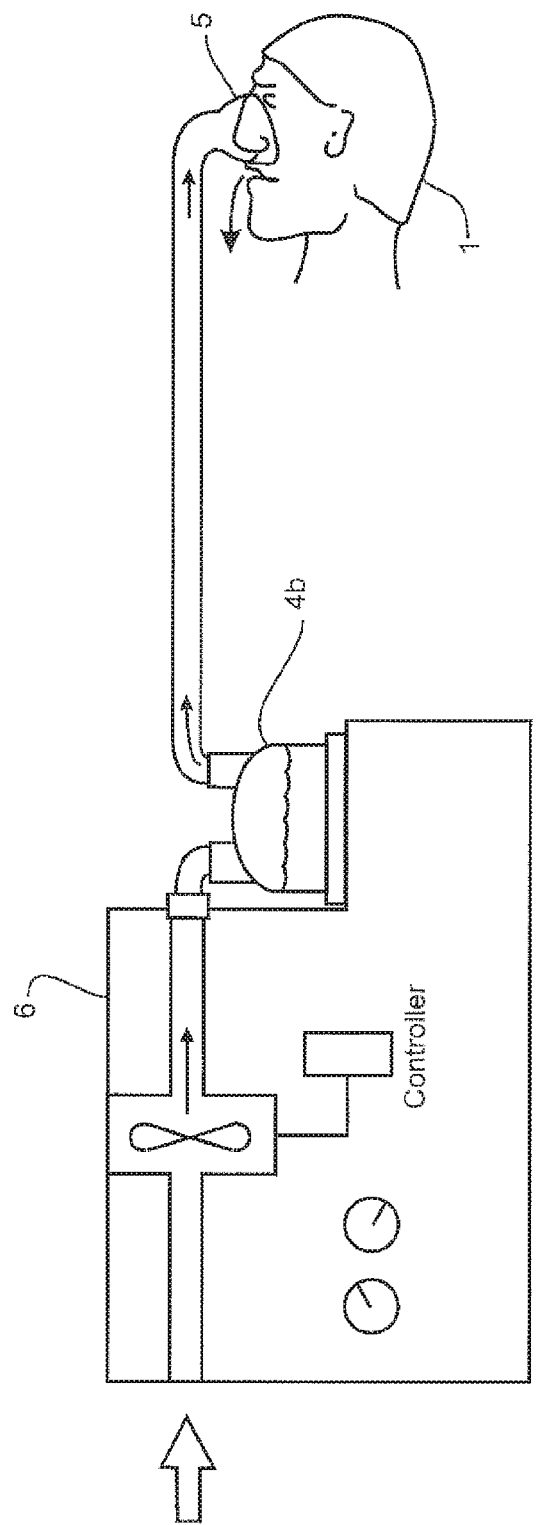
FIG. 2 shows a schematic view of a modular assisted breathing unit and humidifier system.
Figure 3:
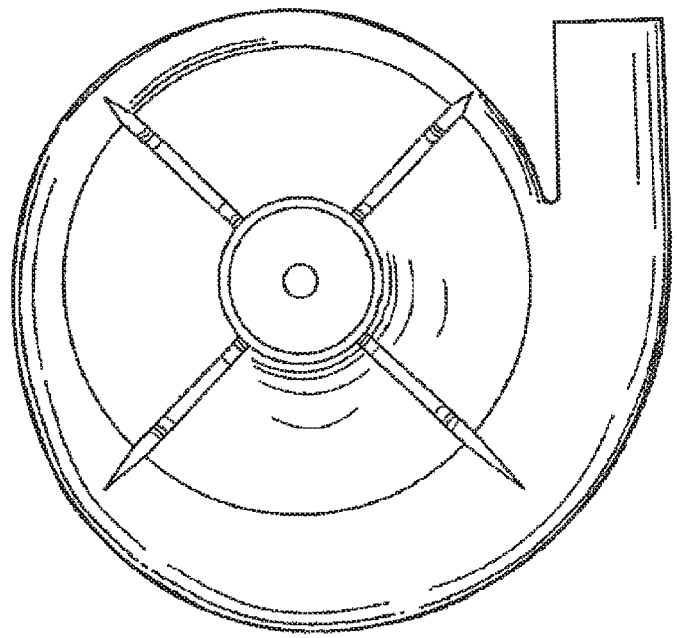
FIG. 3 shows a plan view of an example of a blower unit.
Figure 4:
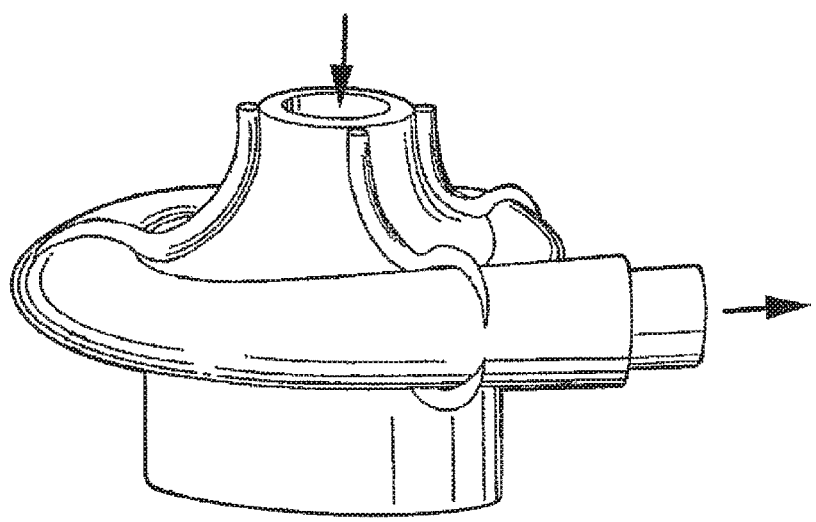
FIG. 4 shows a side view of the blower unit of FIG. 3.
Figure 5:
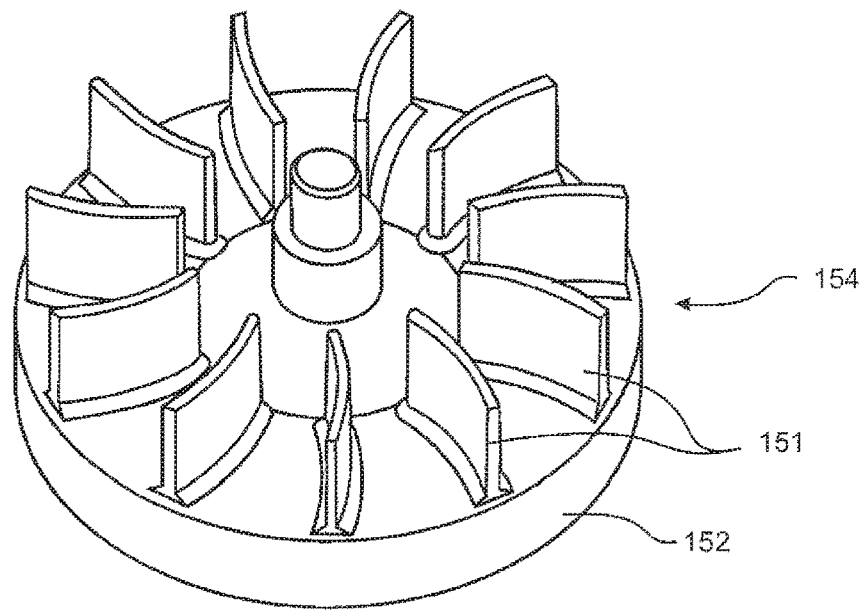
FIG. 5 shows a profile view of an impeller.
Figure 6:
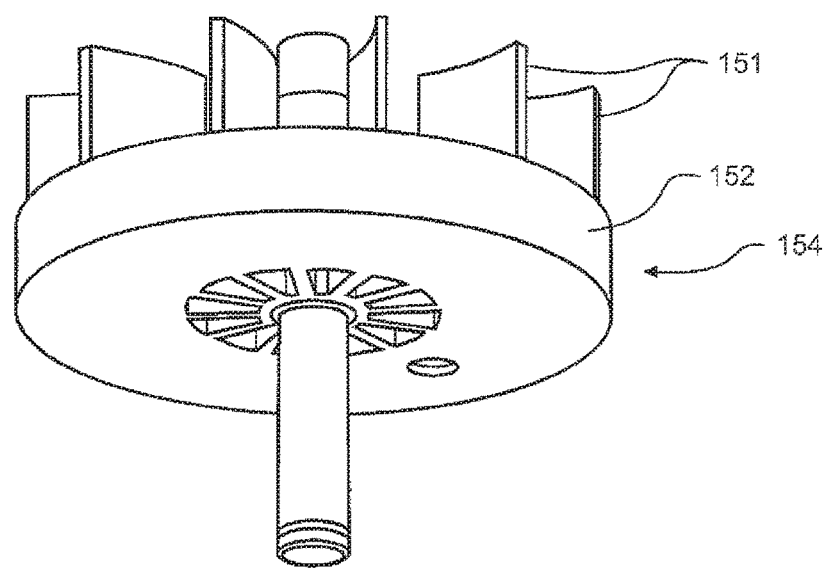
FIG. 6 shows another profile view of an impeller.

The preferred form of the impeller is shown in FIGS. 14 and 15. The impeller 24 has a plurality of blades 31 extending outward from a central hub 32. The impeller is a centrifugal impeller. The hub 32 defines the axis about which the impeller rotates. Preferably the hub 32 has an aperture or recess on the underside to allow engagement with a motor shaft which facilitates impeller rotation. However, other engagement mechanisms, such as over moulding of the hub with a shaft, could be used. When the impeller is rotated, air enters the impeller blades in the region proximate the hub 32, travels radially outward and exits the blades proximate the blade tips 33. The impeller is preferably made in one piece ("one piece construction"), as opposed to moulded in multiple parts and joined. This is possible when there is no shroud—or at most one shroud. This reduces misalignment of components that might lead to imbalance or other disadvantages. In the preferred embodiment there is no shroud (in contrast with for example the shroud 152 shown in FIGS. 5 and 6.)

The blades 31 preferably provide a substantially flat surface, from the hub 32 to the blade tip, and incident the direction of rotation to thereby centrifuge gases. Preferably the tips of the impeller blade tips 33 partially curve in the direction of impeller rotation ("arrow "A"). That is, the blade tips 33 are forward swept. Forward swept blade tips help to impart stronger rotational forces on the gases flowing through the impeller than straight or backswept blades. The forward swept blade tips help to produce a high pressure annulus between beyond tip of each blade. The inner portion 31 of the impeller blade may be somewhat backswept. A backswept blade allows for some recirculation of gases on the blade surface itself. The backswept inner blade portion may be beneficial to increase pressure generation and allow for stable low and reverse gases flow.

Figure 14A:
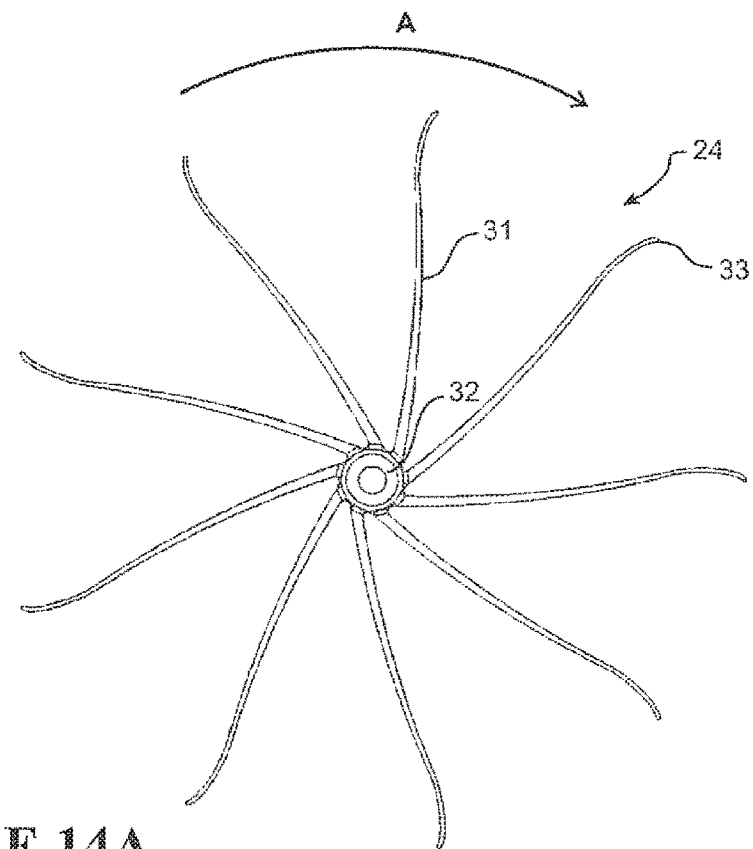
FIG. 14A shows a plan view of the impeller with no shroud according to one embodiment.
Figure 15A:
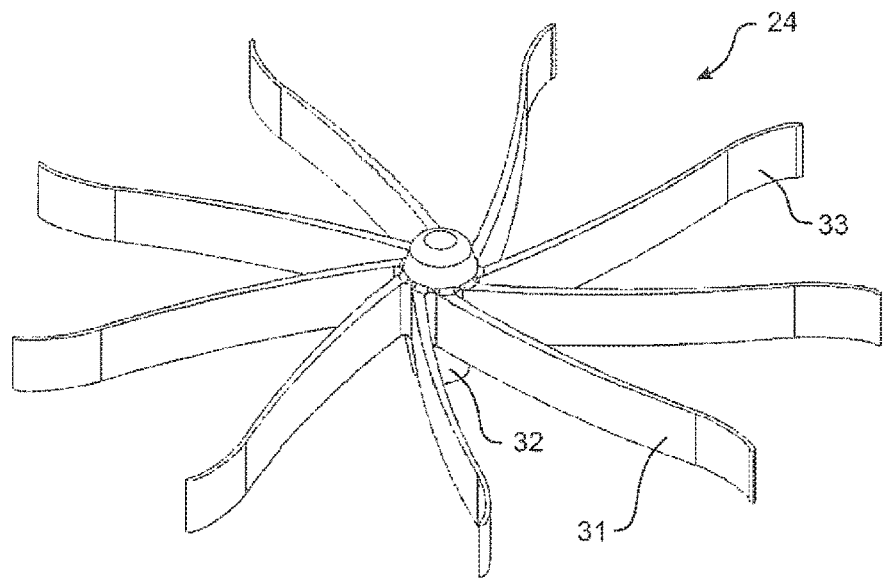
FIG. 15A shows a profile view of the impeller of FIG. 14a with no shroud.
Figure 14B:
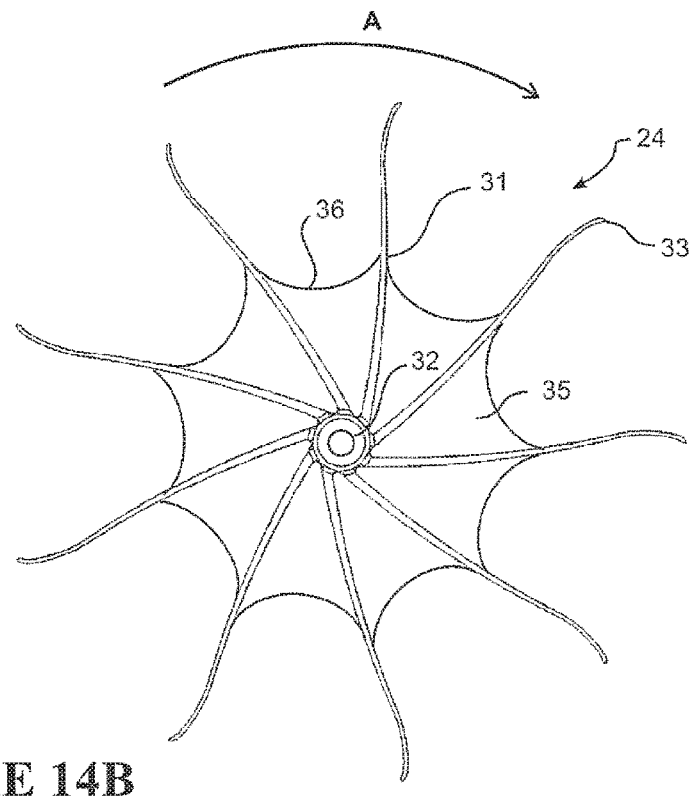
FIG. 14B shows a plan view of the impeller with reduced shroud material according to one embodiment.
Figure 15B:
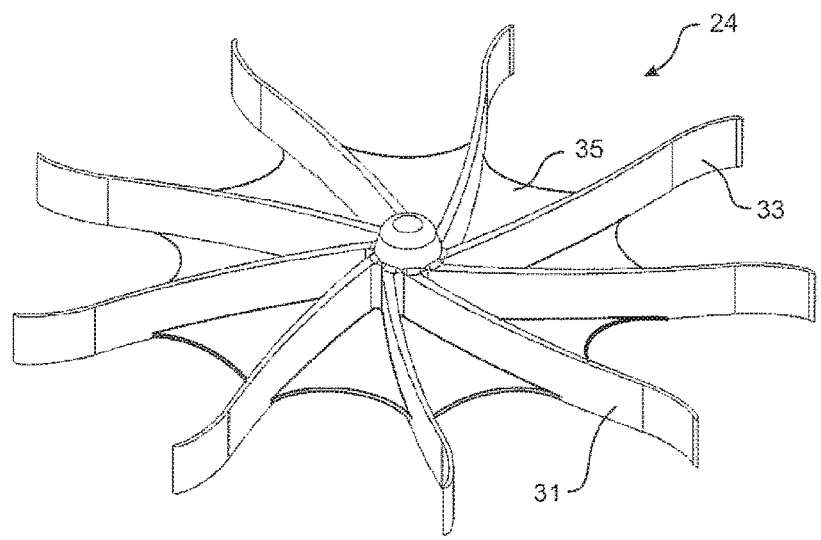
FIG. 15B shows a profile view of the impeller of FIG. 14b with reduced shroud material.
Figure 14C:
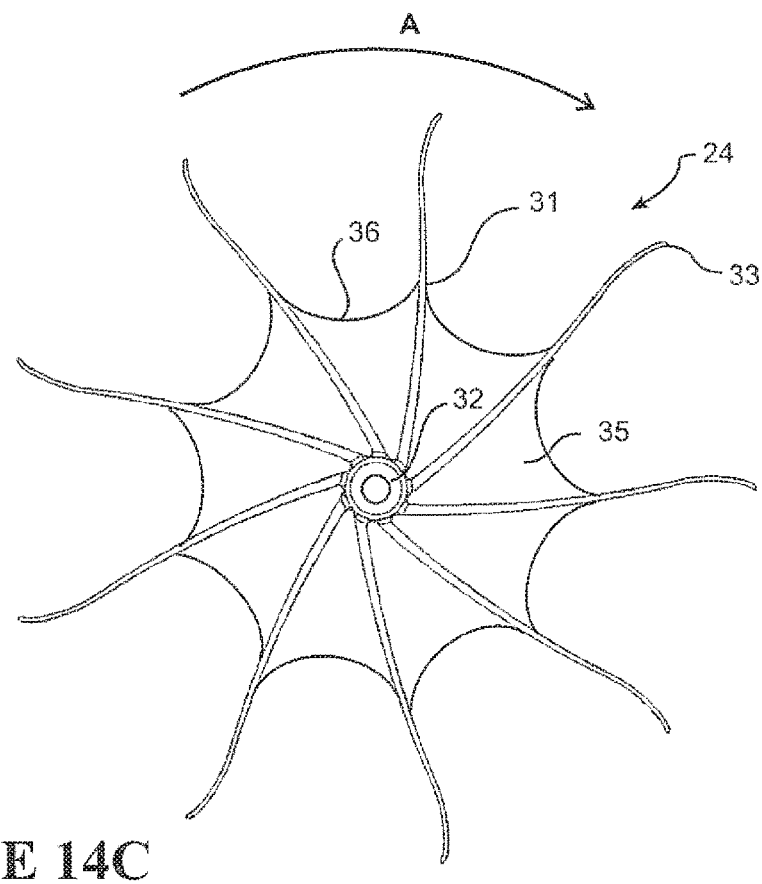
FIG. 14C shows a plan view of the impeller with a web structure.
Figure 15C:
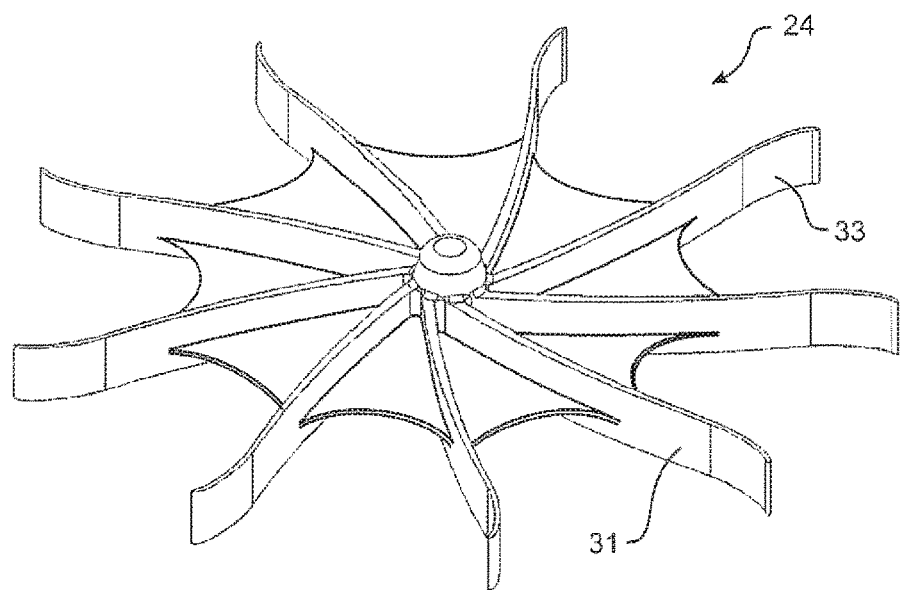
FIG. 15C shows a profile view of the impeller of FIG. 14c with a web structure.

The impeller is constructed to be lightweight. Preferably, this is by making the impeller shroudless, or at least partially shroudless, thereby removing weight. To achieve a lightweight impeller, as shown in FIGS. 14a and 15a, each of the blades 31 of the preferred impeller 24 are open between the blades (that is, the upper and lower "faces" or "planes" of the impeller are open to the internal surfaces of the housing of the fan unit 20) thereby defining a shroudless centrifugal impeller. By omitting a shroud on both the upper and/or lower faces of the impeller blades, the weight of the impeller 24 can be substantially reduced. The weight of the impeller can also be reduced in other ways, in addition to or alternatively to omitting the shroud. For example, a lightweight material can be used. Also, thin blades with minimal material and large gaps between blades could be implemented to reduce weight. Alternatively, a shroud 35 with some of the material removed, such as shown in FIGS. 14b, 15b could be used. A scalloped shaped 36 shroud is provided whereby some of the material between blades 31 is removed. Any suitable amount of material could be removed. A shroud channels air from the impellers. Where significant material is removed, the resulting structure may in fact no longer carry out this function of a shroud but rather just provide support for impeller blades 31. In this case, the impeller 24 may still be considered shroudless, despite having some structure between impeller blades 31. In yet a further embodiment shown in FIGS. 14c, 15c the structure between the impeller blades is a webbing that is disposed centrally between impellers. Such as structure does not function as a shroud. The reduced material structure or webbing 36 can be of any shape (not just scalloped) or extent, of which FIGS. 14b, 15b, 14c, 15c show two examples. A lightweight impeller 24 provides benefits such as manufacturing cost, low rotational inertia and is balanced or requires little effort to rotationally balance once manufactured. An impeller with low rotational inertia can be quickly accelerated and decelerated. A lightweight, shroudless impeller is therefore suited for quickly responding to fluctuating pressure requirements, such as the normal inhalation and exhalation cycle of a patient connected to the breathing assistance device in which the impeller operates.

Figure 29A:
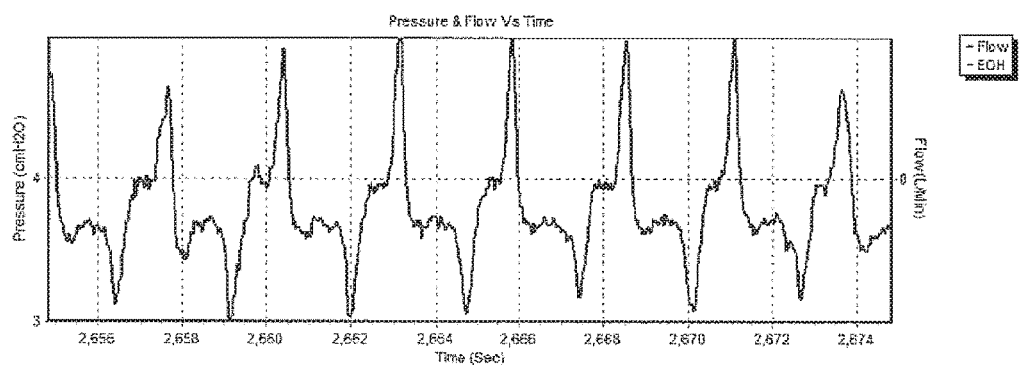
FIG. 29A is a pressure response graph of an earlier blower unit.
Figure 29B:
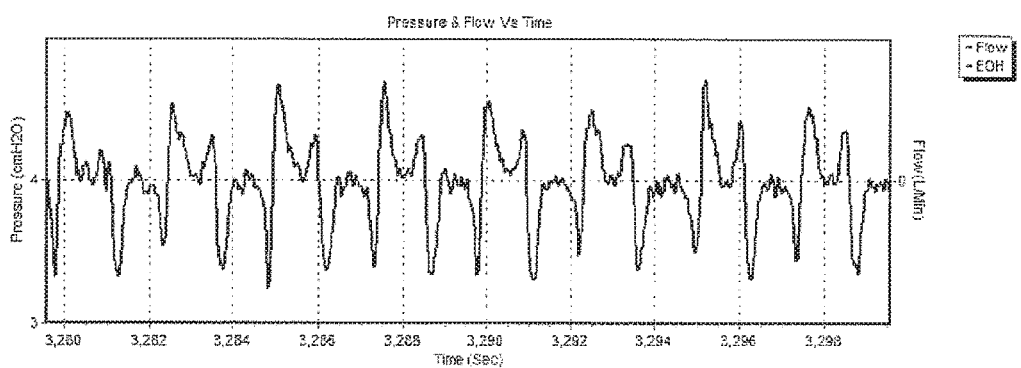
FIG. 29B is a pressure response graph of the blower unit of the present invention.

For example, a conventional shrouded impeller commonly used on a breathing assistance device, weighing approximately 17 grams and having inertia of 6 kg·mm2, can respond to pressure fluctuations of 10 cmH2O in approximately 2 seconds. By contrast, the preferred impeller, weighing approximately 1.7 grams and inertia of 0.5 kg·mm2, responds pressure fluctuations of 10 cmH2O in approximately 100 ms. FIG. 29A shows a graph of pressure verses time for the earlier impeller weighing 17 grams. The impeller is operated to attempt to maintain a constant pressure of 4 cmH2O during the normal inhalation and exhalation cycle of a patient. In comparison, FIG. 29B shows a graph of pressure verses time for the preferred impeller 24. It can be seen that the decrease in mass and rotational inertia over the earlier impeller exhibits much less pressure fluctuation that the impeller of FIG. 29A. The reduced pressure fluctuation is less disruptive to a patient's breathing process, and therefore advantageously increases patient comfort.

As mentioned, the lightweight can be achieved by omitting a shroud. However, it is not necessary to omit the entire shroud—rather just sufficient shroud to bring the weight of the impeller to a suitable level—such as shown in FIGS. 14B, 15B, 14C, 15C. Therefore, lightweight can be achieved by having as much open space (area or volume) between the blades as possible. The open space can be defined in terms of the blade volume to blade sweep volume ratio/percentage. That is, the blades sweep a volume X when rotating and the blades themselves have a combined volume Y (which is the volume of each blade combined). Alternatively, from a plan perspective, the open space can be defined in terms of the blade area to the blade sweep area. The ratios should be kept as low as possible. In one embodiment, for example the swept volume of the impeller is approximately 19,000 mm3, where the blades constitute a volume of approximately 1,200 mm3. The ratio of swept volume to blade volume is therefore approximately 16:1, thereby defining an impeller that is lightweight compared to the smaller, more densely designed and heavier impellers used earlier.

The lightweight impeller can have a weight for example of less than 2 grams and preferably between 0.8 and 1.8 grams, or more preferably, between 1.2 and 1.7 grams, or even more preferably 1.7 grams. These are just examples or a preferred embodiment and the impeller need not be this weight, but some other weight that renders it lightweight.

Alternatively, a lightweight impeller can be designed to remove as much of the shroud as necessary to bring the moment of inertia to radius ratio down to preferably less than 15 gram*mm, and more preferably between 8-12 gram*mm and in one possible embodiment approximately 11 gram*mm. For example, in one possible embodiment, such an impeller can have a radius of 35 mm, a circumference of 219 mm, and at 15,000 rpm a moment of inertia of 344.22, a tip speed of 54.98 m/s, a pressure of 1,800 Pa and a tip speed to inertia to radius ratio of 3.5 or more and for example 5.59. More generally, a lightweight impeller could have dimensions/parameters within the following ranges (note these ranges are indicative—not limiting): radius: 15 mm-60 mm; and/or weight: less than 2 grams.

A pressure ratio to inertia to radius ratio of greater than 50:1 Pascals per gram*mm and preferably 80:1 Pa per gram*mm or more at 1,000 Pa.

Lightweight impellers enable larger radius impellers to be used. Yet larger radius impellers can be used than those mentioned above. Larger radius impellers provide greater tip speed and pressure. The construction of the impeller allows for greater radius impellers because the lightweight nature of the impeller is such that even with larger impellers, the inertia is still low enough to provide the required response and pressures.

The lightweight nature of the impeller can be achieved through removing mass through any suitable means, such as removing the shroud and/or material from the impeller and/or using lighter materials. One possible manner in which to reduce impeller mass is to reduce the number of blades.

The impeller generates a high pressure annulus between the tip and inner face of the housing. The backward facing impeller with a forward sweep at the tip also allows for recirculation on the blade itself, which helps with increased pressure generation and stable flow and reverse flows.

Figure 16:
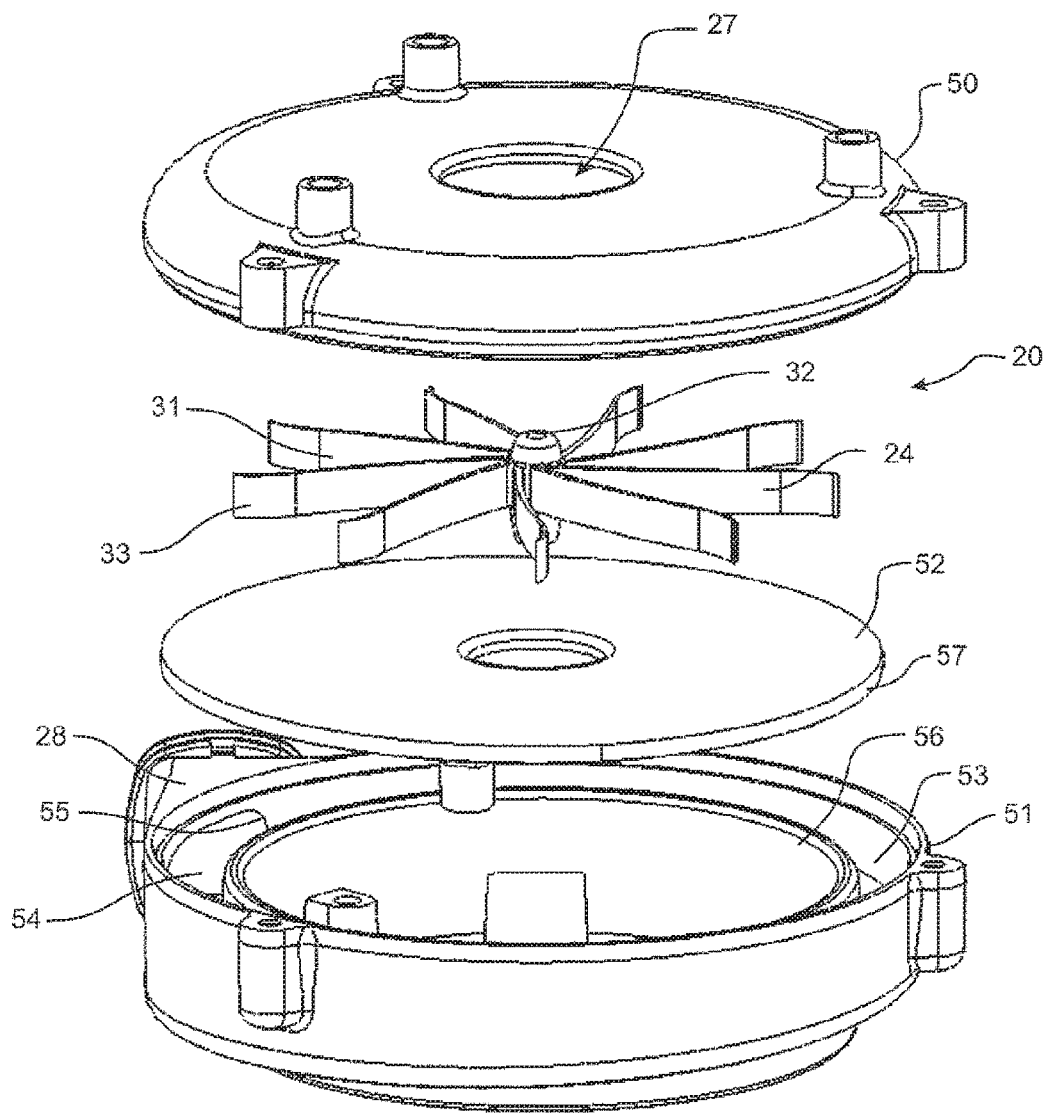
FIG. 16 shows an exploded view of the preferred housings and impeller of one embodiment.

The fan unit 20 as shown in FIGS. 11 and 12 and described above is shown in exploded form in FIG. 16. The blower has an upper housing layer 50 and a lower housing layer 51 that assemble to encapsulate a partitioning layer 52 and the impeller 24. The blades of the impeller are open to the internal surfaces of the upper and lower housing layers. The partition layer 52 and the inner surface of the upper layer 50 are profiled to substantially enclose the impeller blades when the layers are assembled. This forms a first interior region ("upper region"). The upper housing layer 50 has the aperture 27 that defines the gases entry into the blower. The lower housing layer defines a volute 53 where gases are collected before emission from the blower. Preferably the volute 53 also has a sealing inner wall 56. The wall 56 defines a space internal to the lower housing that may be used to house a motor. The lower housing layer 51 and the partition 52 form a second interior region ("lower region").

The outlet passage 28 of the fan unit 20 is connected to the volute 53 via an aperture 54. The aperture 54 and the volute wall 53 define a tongue 55 whereby gases circulating in the volute 53 are diverged into the outlet passage 28.

The partition layer 52 is generally circular and substantially divides the upper housing 50 from the lower housing 51 thereby defining the upper and lower gases flow (interior) regions of the blower. To allow gases to flow from the upper region to the lower region an aperture (opening) 57 is located at, or close to the outer edge of the partition. The aperture 57 is shown more clearly in FIGS. 17 and 18. The aperture 57 is most preferably an opening formed by a cut-away in the partition layer 52, or some other configuration/shape of the housing 51 such that the combination/arrangement of the partition layer 52 and the housing 51 creates an aperture/opening between the two. However, the aperture 57 may also comprise a flow path formed separately to the partition layer, such as a bulge or fluid channel formed in the walls of the upper 50 and lower housings 51. The cut-away could form a circumferential aperture 57 between the housing 51 and partition 52, for example. The curvature/centre of radius of the circumferential aperture 57 is preferable offset from the centre of radius of the partition 52 or otherwise has a curvature that differs from that of the circumference of the partition 52 resulting in an eccentric or otherwise offset circumferential aperture 57 around the circumference of the partition 52 as shown in the Figures. This produces an aperture 57 with a crescent ("smile") shaped opening that spans a leading edge 58 to a trailing edge 59. However, the aperture may be of any shape with a gradual opening and closing relative to the plane of impeller rotation. The aperture allows for gradual supply of pressure and flow from the high static pressure source at the top of the blower. The angle of the aperture opening and closing is tuned to allow for reverse flow to return through the system in a stable fashion. It also contributes to the blade pass noise reduction by not having a sharp break in geometry. The aperture provides addition tongues, as well as that on the outlet. The gradual opening and closing of the aperture ("tapers") provides tongues. The maximum velocity at the outlet (e.g. 10 m/s) is less than that at the tapers (e.g. 60 m/s). The gradual opening and closing with blades passing at that speed manages blade pass noise. The width and length of the aperture 57 controls the velocity in the lower (volute) section of the housing. A wider and longer aperture increases velocity in the volute, for example.

Figure 17:
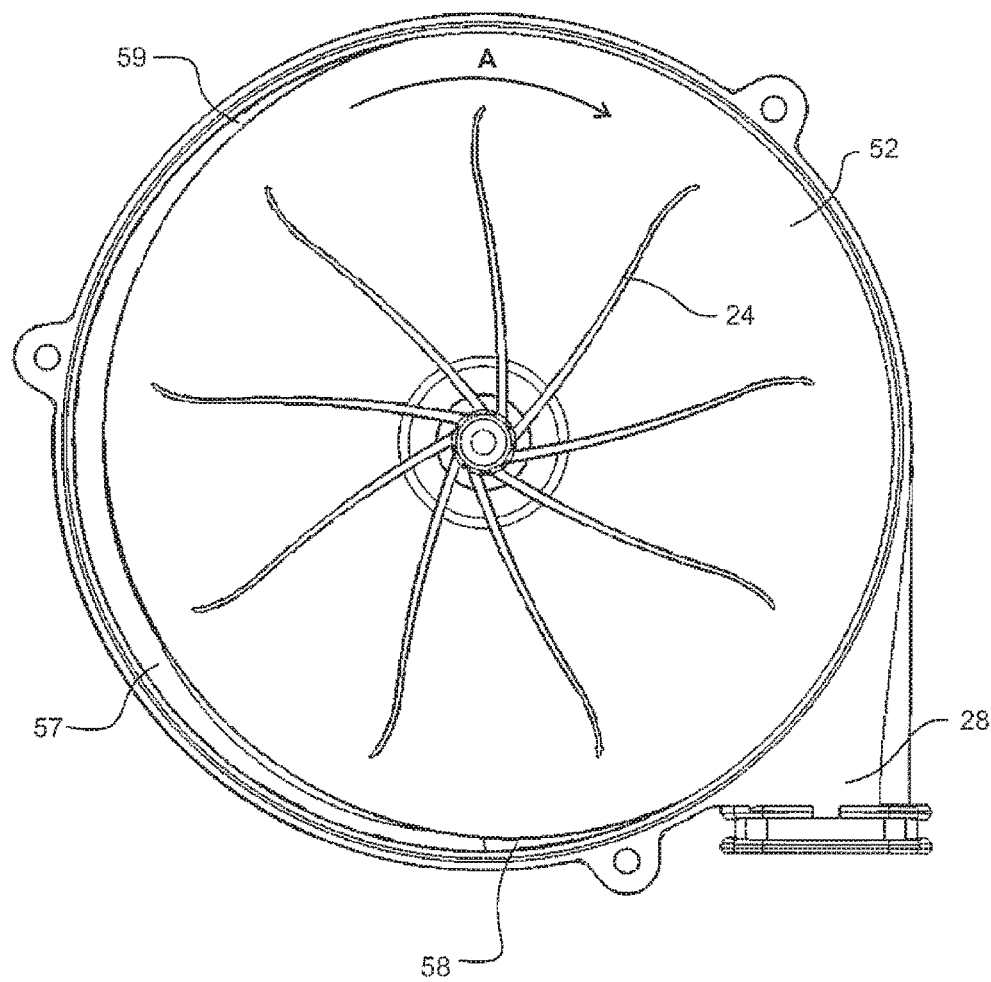
FIG. 17 shows a plan view of the lower housing, partition and impeller of one embodiment.
Figure 18:
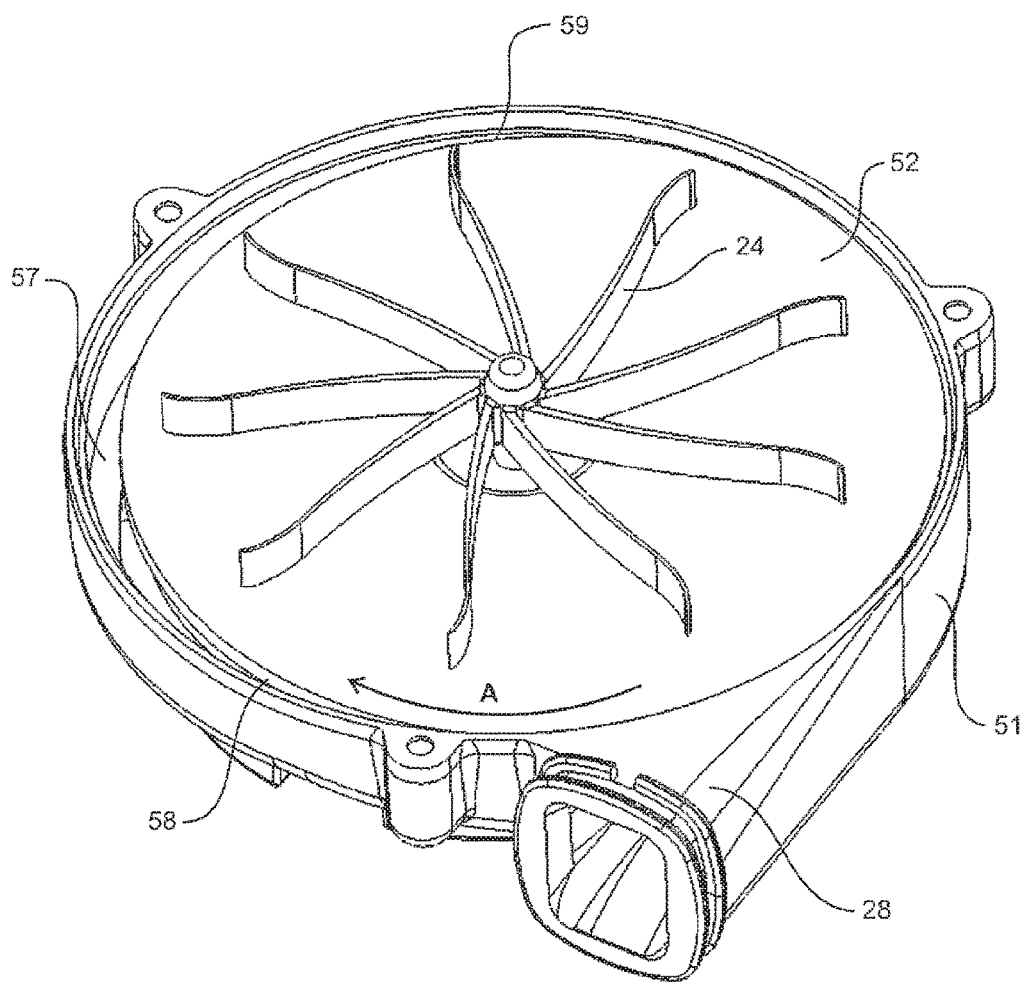
FIG. 18 shows a profile view of the components of FIG. 17.

During operation of the blower, the impeller 24 is rotated in direction A—see FIG. 17. The rotation of the impeller 24 draws gases through the inlet 27 and through the blades 31 toward the outer wall of the upper housing layer 50. During operation, air B can also be drawn through the stator/rotor from the other side of the housing—see e.g. FIG. 13. The air B drawn through can cool the motor. The shroudless impeller 24 enables air to be drawn through the motor in this manner thus providing cooling. The forward swept blade tips 31 impart strong rotational forces to the gases circulating in the upper region of the blower housing to thereby create high circulating gas speeds. Gases in the upper region will naturally flow through the aperture 57 to the lower region due to pressure differential between regions. When the gases in the upper region, having a high velocity and low pressure, enter the lower region, specifically the volute 53, the gas velocity drops and the pressure increases. Typically the volute 53 has a greater volume than the upper region to help facilitate a gases pressure increase.

By dividing the blower internal space into two separate regions a number of advantages can be realised. In a conventional blower, high velocity gases leaving the impeller are incident to the edge, or tongue, that defines a physical boundary where gases are split from the volute to enter the outlet passage. High velocity gas flow at incident the tongue is turbulent and inefficient to blower performance. The turbulence caused by the tongue reduces also introduces a source of noise. In contrast, dividing the housing of the preferred blower into the upper and lower regions reduces the impact caused by the tongue. The upper region allows the gases to circulate at a high speed. The gradual radial opening and closing of the preferred partition 57 provides a fluid path to the lower region that is free from (or has reduced) aerodynamically turbulent edges. When circulating gases have entered the lower region, the enlarged volume of the volute encourages the gases to slow and increase pressure. The reduced gases velocity reduces the impact of turbulence normally caused by the tongue 55 to a low or negligible level. The blower unit is therefore able to operate across a wide pressure and flow range with substantially reduced noise output when compared to other blowers. A wider and longer aperture 57 increases the flow rate of the lower region relative to the upper region. Therefore, the size of the aperture is selected according to the desired flow rate and pressure range of the blower unit.

Figure 19:
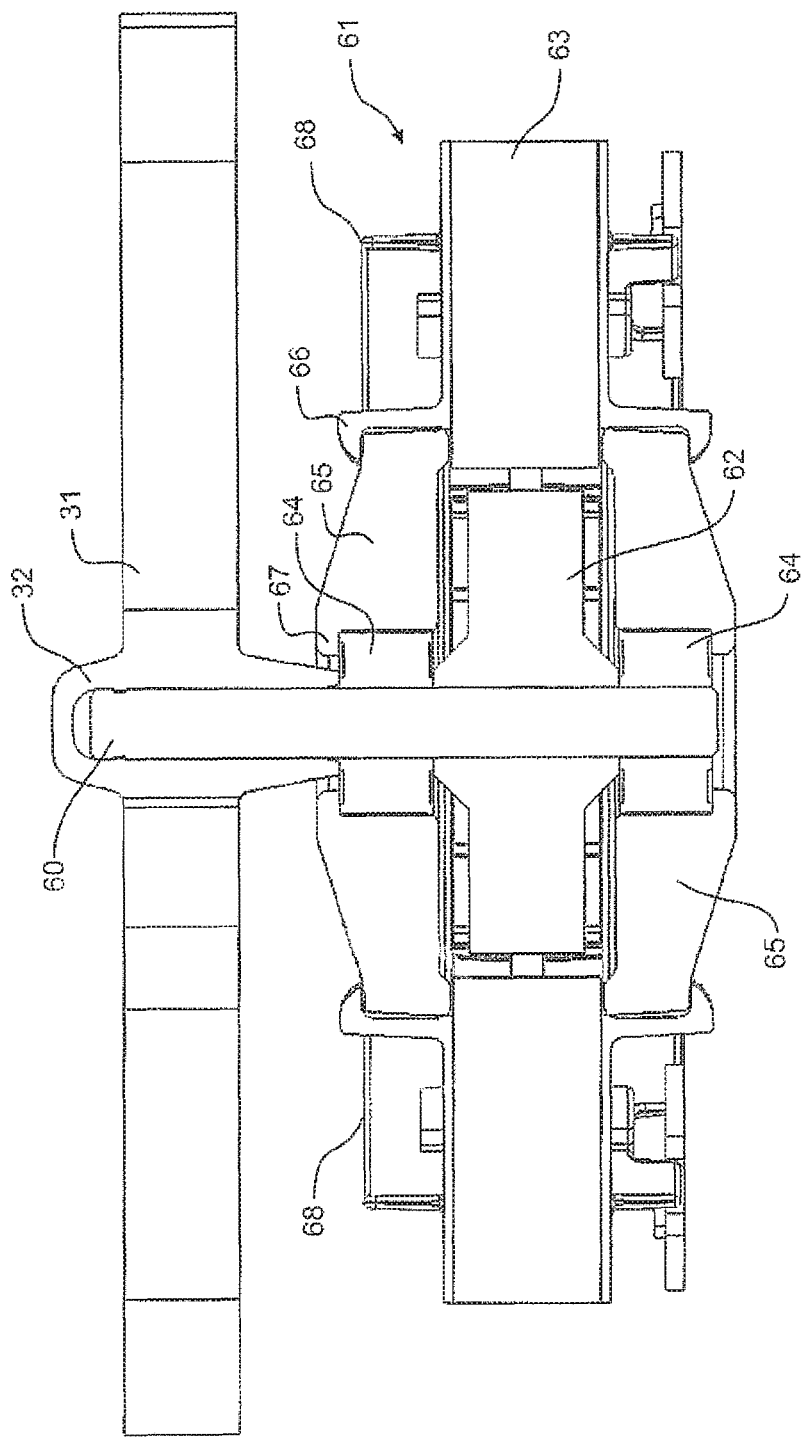
FIG. 19 shows a cross sectional view of the motor and impeller of one embodiment.

The motor used to drive the impeller 24 is shown in cross section in FIG. 19. Preferably the motor is a brushless DC motor operated using sensorless vector control (also termed "field oriented control") controlled by a microcontroller, microprocessor or similar controller 14 (such as shown in FIG. 7), for example, via the connector 131 mounted to a PCB 130. The control can be tuned to suit a low inertia impeller. The central hub 32 of the impeller 31 is engaged with a shaft 60 that extends from the motor 61. Mounted to the shaft is a plurality of, preferably small, magnetic segments to form a rotor 62. In one embodiment the magnet is 20 mm in diameter, but more generally the diameter could be less than 20 mm and preferably between 10 mm to 15 mm. The magnet volume is less than 1600 mm3 and can be between 500 mm3 and 1600 mm3. Surrounding the rotor 62 is a laminated stator having a plurality of poles 63 and windings 68. The stator is mounted to the PCB or other substrate 130 and the windings coupled to the connector 131. The windings are selectively energised by the microcontroller 14 via the connector 131 to facilitate rotation of the rotor, and therefore the shaft 60 and impeller 31, about the central axis defined by the centreline of the shaft 60.

The shaft 60 is held within the motor by a bearing structure. Preferably the bearing structure has one or more bearings 64 and one or more bearing mounts 65. The bearing mounts 65 as shown engage with the bearings on an inner surface and with the stator on an outer surface. The preferred engagement of the mount to the bearings and the stator is frictional. To promote a frictional engagement, the bearing mounts 65 are made of a soft, yet resilient and/or flexible material such as silicone rubber or other elastomeric material. The material can be low creep, temperature stable, low compression set with a high tan delta (highly viscous), highly damped. Examples comprise: Dough Moulding Rubbers like—NBR, Nitrile and Flouro silicone; Thermo Plastic Elastomers (TPE's) like Santoprene by Exxon; Thermo Plastic Urethanes like Dynaplast by GLS Corporation; Heat Cured Casting Urethanes like 10T90 by National Urethanes; and multiple other cold cast rubbery compounds like RTV (Room Temperature curing Vulcanites) by Dow Corning, Whacker and others. In another embodiment, bushings (rubber or otherwise) could be used instead of bearings.

Such materials allow the mounts 65 to compress when installed, then expand into their chosen location to be held in place by engagement expanded dimension with a restriction. The mounts 65 are optionally restrained by an overhang 66 formed as part of an electrical insulator/isolator or other frame structure ("stator frame") on the stator. Similarly, the bearings may be restrained by an overhang 67 formed as part of the bearing mount. Either or both of the overhangs may be discretely positioned about the inner and outer annulus of the bearing mounts, or alternatively, extends around the circumference of the mount to define a recess in which the mount is located.

The bearing mounts provide compliance to the rotatable shaft 60. As rotatable objects, such as the rotor 62, shaft 60 and impeller 31 usually suffer from some degree of rotational imbalance, the bearing mounts are able to isolate inherent rotation induced vibration from the motor rotor. It has been found that combination of the lightweight, shroudless impeller having a low rotational inertia, as described above, together with the given compliance of the bearing mounts enables the rotor 62, shaft 60 and impeller 31 to be manufactured and any post manufacture balancing process for the rotating components entirely omitted. These advantages benefit manufacturing costs and time. The lightweight nature of the impeller allows any imbalances to be compensated by the bearing mounts. A lightweight impeller also allows faster speed response of the impeller to changing conditions. Any unwanted fluctuations in pressure due the lack of shroud can be compensated for by quickly changing the impeller speed to return pressure to the desired level.

It should be noted that while FIG. 19 shows the bearing mounts 65 mounted within the motor stator, they may equally be housed externally to the motor. For example, the mounts 65 may instead be mounted within journals formed within the blower housings, or the gases supply unit 7. In such circumstances where the bearing mounts are located within the gases supply unit 7, it may also be advantageous to omit discrete structures for the blower housing 50, 51, instead mounding the inner surfaces of the housings directly to the internal structure of the gases supply unit 7.

Figure 20:
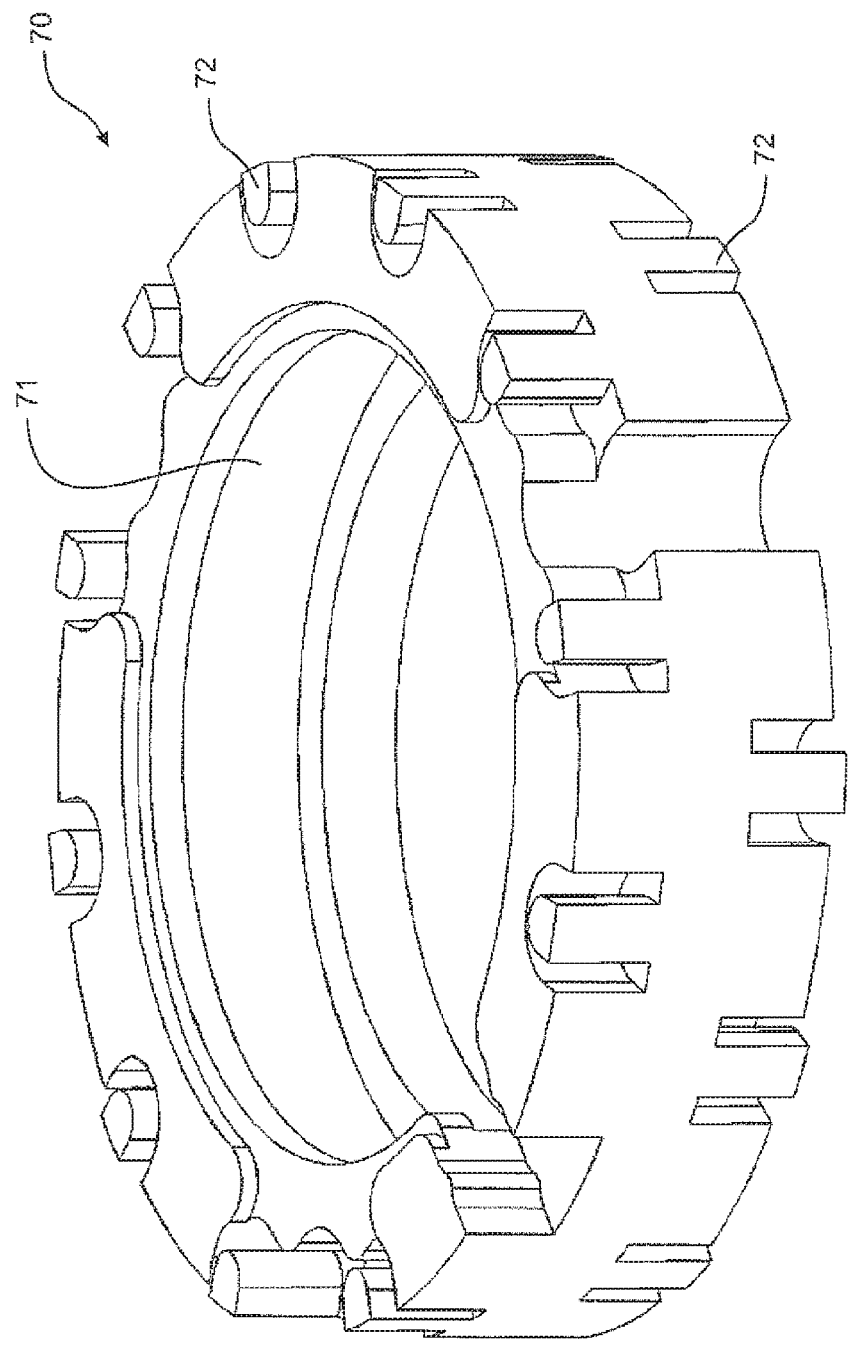
FIG. 20 shows a motor mounting structure one embodiment.
Figure 21:
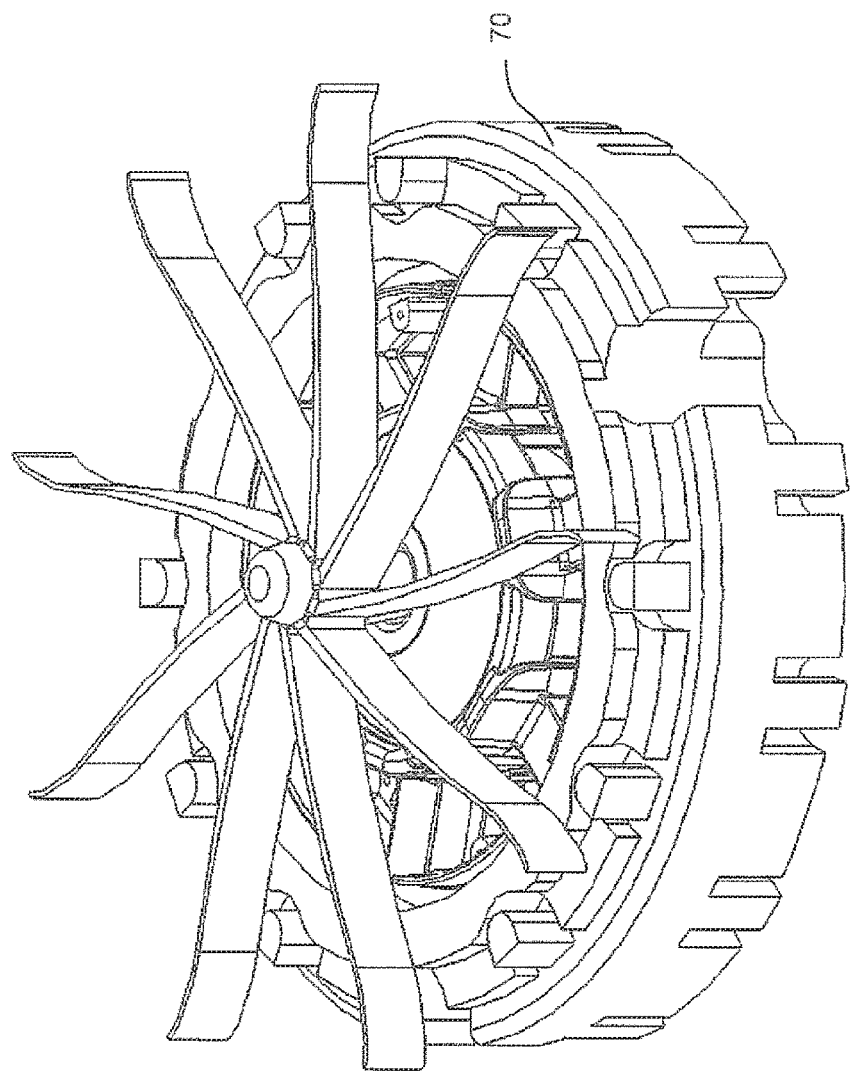
FIG. 21 shows the motor mounting structure with a motor and impeller of one embodiment.

To provide further vibration damping of the rotational components of the blower, the motor and impeller, can optionally be mounted on a compliant mounting device. FIG. 20 shows one embodiment of such a mounting device 70. In accordance with the preferred embodiment of the invention the mount is most preferably made from a soft, flexible yet resilient material such as silicone rubber. The mounting device 70 has an internal recess 71 in which the stator is relieved. Preferably the internal recess is smaller than the outer surface of the motor to encourage an interference fit between these components. FIG. 21 shows the motor 61 positioned within the mounting recess 71.

A plurality of projections 72 encircles the upper and lower surfaces of the mount 70. Each projection 72 preferably has a base recessed into the body of the mount to effectively increase the length whereby the projections are free to bend. The end of projection extends past the upper and lower surfaces of the mount to provide supporting leverage to the mount and motor assembly. During operation of the motor, vibration caused by any imbalance of the rotational components is absorbed by each of the projections by allowing the body of the mount 70 to move relative to the surface on which the projections 72 are supported.

Figures 22A, 22B:
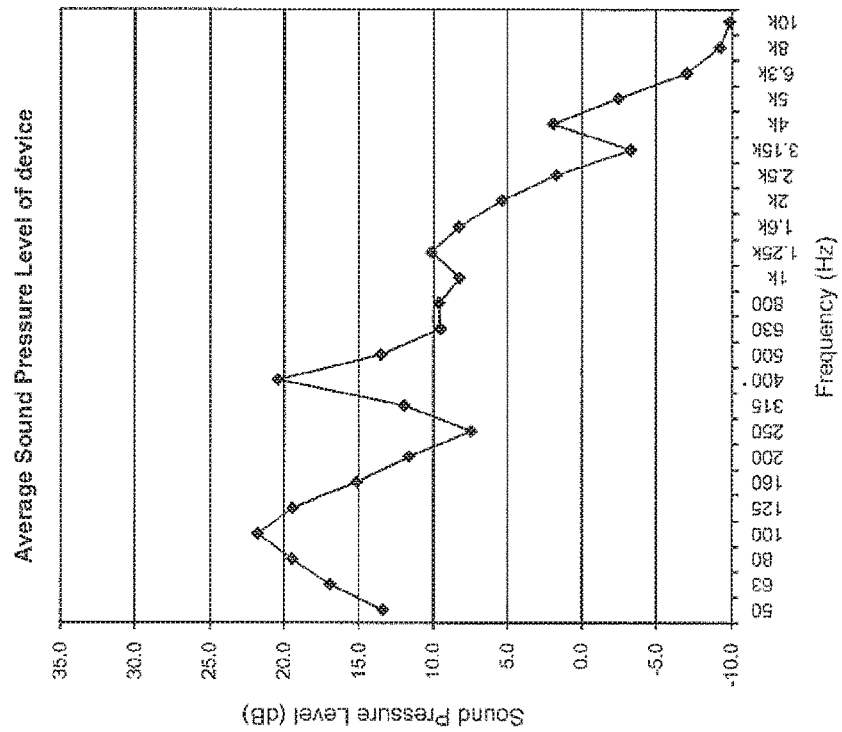
FIG. 22A is a graph of average sound pressure levels of an earlier blower unit.
FIG. 22B is a graph of average sound pressure levels of the blower unit of the present invention.

FIG. 22A is a graph of the sound pressure level of a conventional fan unit tested in an anechoic chamber. FIG. 22B is a graph of the sound pressure lever of a fan unit according to the present invention. It can be seen that the lightweight and shroudless impeller 24, the flexible bearing mounts 65 and flexible motor mount 70 contribute to a significantly reduced noise output across the tested spectral range of 50 Hz to 10 kHz.

Figure 23:
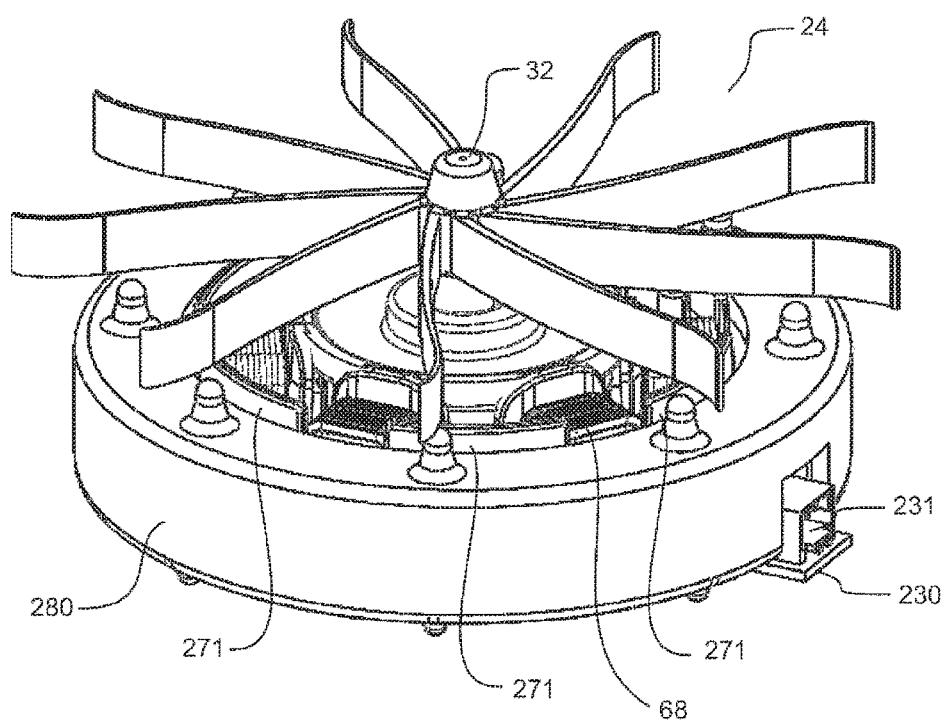
FIG. 23 shows the motor mounting structure with a motor and impeller of a second embodiment.
Figure 24:
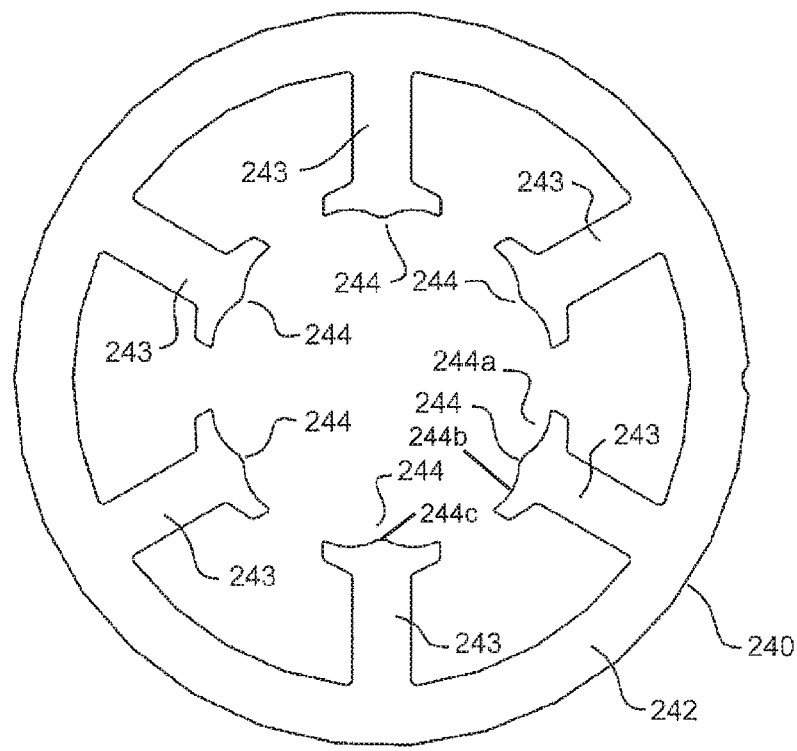
FIG. 24 shows a stator lamination of the second embodiment.
Figure 27:
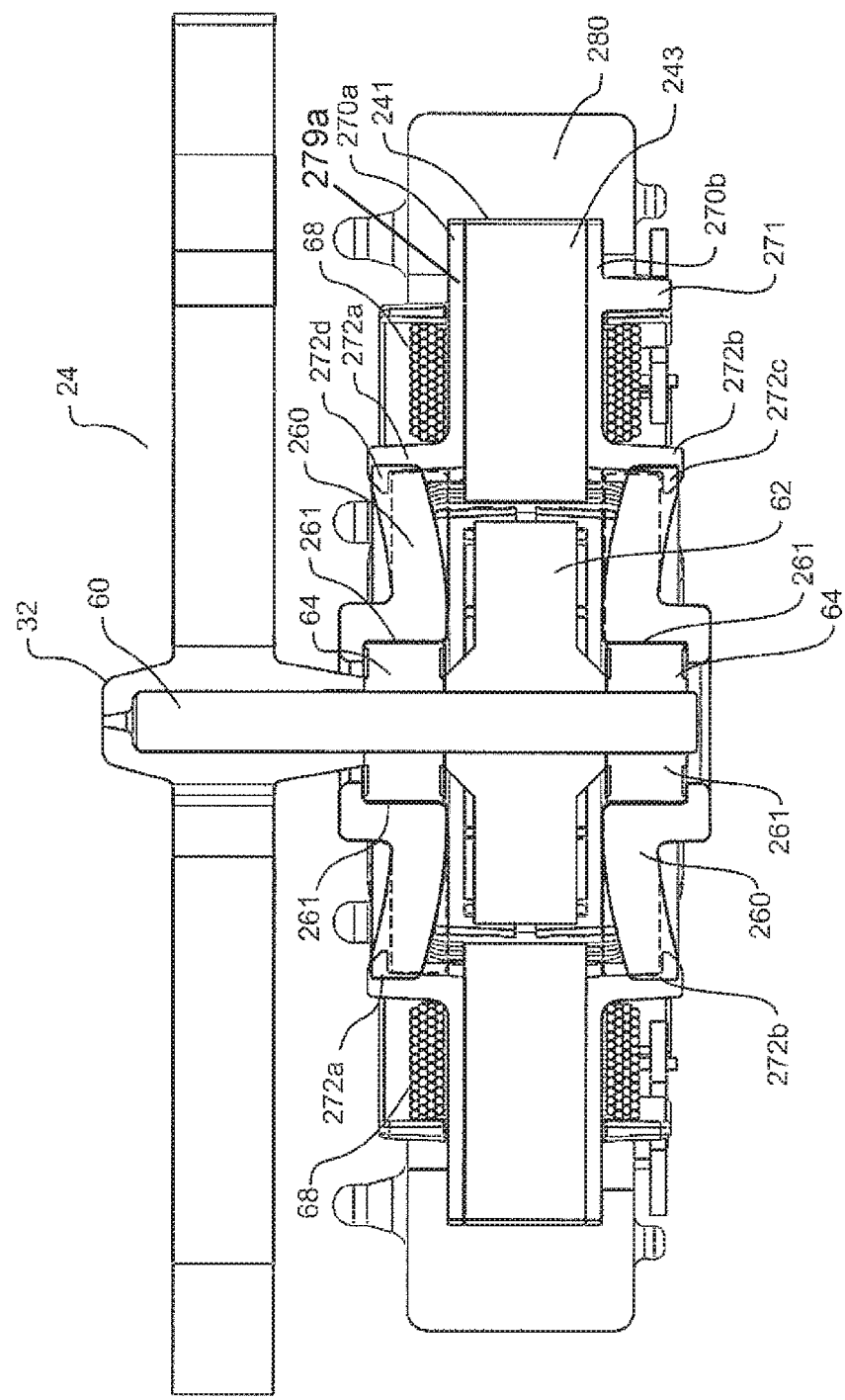
FIG. 27 shows a cross sectional view of the motor and impeller of the second embodiment.

A further embodiment of the motor and impeller assembly is shown in FIGS. 23 to 28. Many aspects of this embodiment are the same as those in the previous embodiment. Features described in relation to the previous embodiment not described in this embodiment can be assumed to exist in this embodiment where appropriate. Like features will use the same reference numerals as the previous embodiment. The motor used to drive the impeller 24 is shown in cross-section in FIG. 27. Preferably the motor is a brushless DC motor operated using sensorless vector control ("field oriented control") controlled by a microcontroller, microprocessor or similar controller 14 (such as shown in FIG. 7), for example, via a connector 231 mounted to a PCB/substrate 230 (such as shown in FIG. 23). The control can be tuned to suit a low inertia impeller. Referring to FIGS. 23, 24 and 27, the central hub 32 of the impeller 24 is engaged with a shaft 60 that extends from the motor 61. Mounted to the shaft is a plurality of, preferably small, magnetic segments to form a rotor 62. Surrounding the rotor 62 is a laminated stator 241 having an annular outer portion 242 and a plurality of poles 243 and windings 68. The stator is mounted to the PCB or other substrate 230 and the windings 68 coupled to the connector 231. The stator 241 has an electrical insulator/isolator (forming a stator frame) 270a, 270b covering the top and bottom of the annular portion 242 and the poles 243. Each winding 68 is preferably assembled on the insulator 270a, 270b over each pole 243. Protrusions for engagement and retainment are provided around the circumference 271 extending upwards and at the end of the poles extending upwards 272a and downwards 272b.

Figure 25:
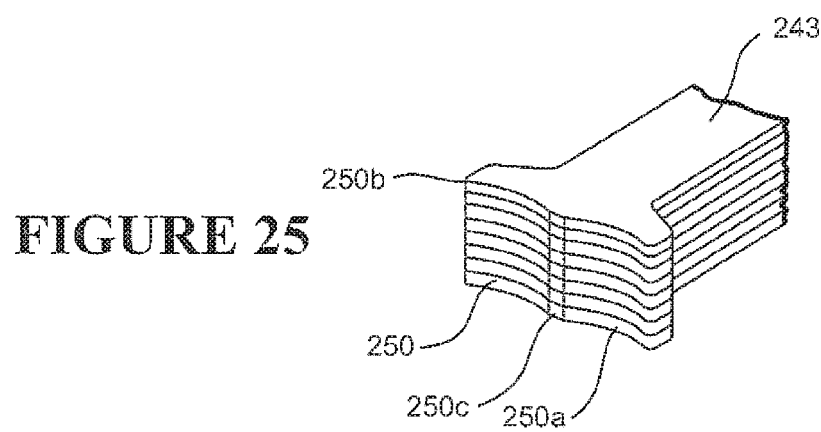
FIG. 25 shows a pole face of the second embodiment.
Figure 26:
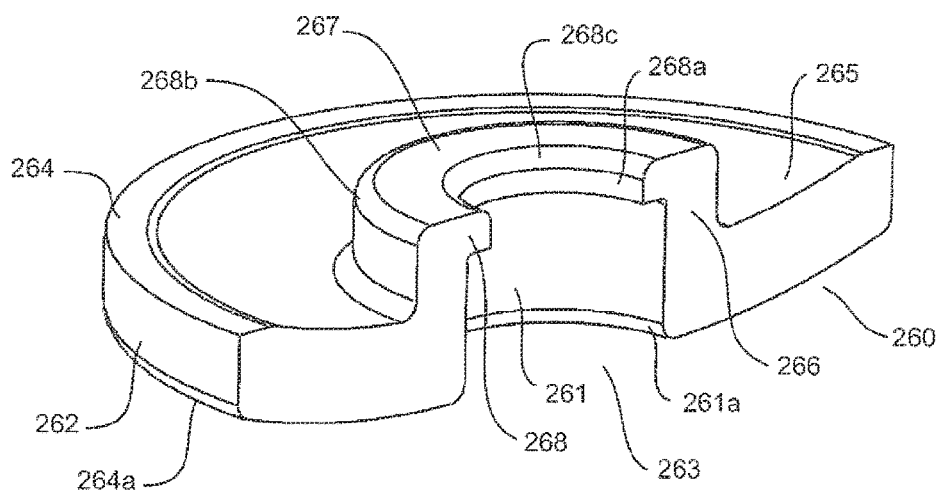
FIG. 26 shows a bearing mount of the second embodiment.

Referring to the plan view of one of the laminations 240 in FIG. 24, each lamination comprises an annular outer portion 242 and a pole portion 243 extending radially inwards. The edge 244 of each pole portion 243 includes a wave shape. The wave shape comprises two concave portions 244a, 244b meeting at a central apex 244c. Referring to FIG. 25, when a plurality of the laminations 240 are stacked to create the stator 241, each pole 243 has an inner radial face 250 with a wave shape as shown in FIG. 25. The face 250 comprises two concave portions 250a, 250b meeting at a central apex 250c. This arrangement reduces cogging. The stator and/or rotor can have a skewed magentisation. The windings are selectively energised using the controller 14 via the connector 231 to facilitate rotation of the rotor, and therefore the shaft 60 and impeller 31, about the central axis defined by the centreline of the shaft 60.

The shaft 60 is held within the motor by a bearing structure. Preferably the bearing structure has one or more bearings 64 and one or more bearing mounts 260 (see FIG. 26). The bearing mounts 260 as shown engage with the bearings 64 on an inner surface 261 and with the stator 241/insulator 270a/270b on an outer surface as shown in FIG. 27. The bearing mount 260 comprises a main annular body 265 that curves from a low point at a central aperture 263 to a higher point at the outer circumference 262. The outer circumference comprises an engaging lip 264, preferably with a chamfer 264a on the intersection of the outer circumference 262 with the main annular body 265. The intersection of the inner aperture 263 with the inner circumference 261 of the main body 265 also preferably has a chamfer 261a. An annular wall/boss 266 extends upwardly from the main annular body 265 at the inner aperture 263. The top portion 267 of the annular wall 266 has an overhanging engagement lip 268. The intersection of the lip 268 with the annular wall 266 and with the overhanging lip side wall 268a are preferably chamfered 268b, 268c. The preferred engagement of the bearing mount 260 to the bearings 64 and the stator 241 is frictional. To promote a frictional engagement, the bearing mounts 260 are made of a soft, yet resilient and/or flexible material such as silicone rubber or other elastomeric material. The material can be low creep, temperature stable, low compression set with a high tan delta (highly viscous), highly damped. Possible materials were described in relation to the previous embodiment. Such materials allow the mounts 260 to compress when installed, then expand into their chosen location to be held in place by engagement expanded dimension with a restriction. They also provide compliance.

FIG. 27 shows the bearing mounts in solid lines in the uninstalled/unassembled state, with an upward curvature. The dotted lines show the bearing mounts 260 in the installed/assembled state, clipped in to the stator/insulator 279a, 270b. In the installed state (also called engaged state or configuration) the annular body is engaged with the stator 241 and/or stator frame 270a, 270b and the annular body 265 is coerced from the curved state (shown in solid lines) into an engaged (flat) configuration (shown in dotted lines) that provides preload to the one or more bearings by action of the bearing mount providing bias provided by the resilient/flexible body acting on the stator and/or stator frame and the bearings. The mounts 260 are optionally restrained by an overhang 272c, 272d formed on the insulator 270a, 270b. Similarly, the bearings 64 may be restrained by an overhang 268 formed as part of the boss 266 on the bearing mount 260. Either or both of the overhangs may be discretely positioned about the inner and outer annulus of the bearing mounts, or alternatively, extends around the circumference of the mount to define a recess in which the mount is located. The impeller/shaft/rotor is assembled into the stator 241 by assembling the bearings 64 on the shaft 60, assembling the bearing mounts 260 on the bearings 64 and manipulating the bearing mounts 260 (by hand, jig or other means) so they engage with the stator insulator 270a, 270b at each pole 243. In an alternative embodiment, the bearing mounts 260 are not coupled directly to the stator or insulator 270a/241 but rather are coupled to another structure such as a housing. Any coupling arrangement with any suitable structure can be provided which provides the required functions as set out below.

The bearing mounts 260 provide compliance to the rotatable shaft 60. As rotatable objects, such as the rotor 62, shaft 60 and impeller 24 usually suffer from some degree of rotational imbalance, the bearing mounts are able to isolate inherent rotation induced vibration from the motor rotor. It has been found that combination of the lightweight, shroudless impeller having a low rotational inertia, as described above, together with the given compliance of the bearing mounts 260 enables the rotor 62, shaft 60 and impeller 24 to be manufactured and any post manufacture balancing process for the rotating components entirely omitted. These advantages benefit manufacturing costs and time. The lightweight nature of the impeller 24 allows any imbalances/misalignment to be compensated by the bearing mounts 260—the arrangement is self aligning due to the bearing mount compliance (due to resilience and/or flexibility, for example). The bearing mount construction, including the geometry and material, also provides axial preload on the bearings, e.g. of up to 7 Newtons. The annular nature of the bearing provides consistent/even preload around the bearing 64. The resilient/flexible curved annular body allows the bearing to be installed in place and provide the preload. The annular nature of the bearing mount 260 provides for even preload around the bearing, while the low creep construction material maintains preload. The material of the bearing mounts 260 is also preferably a viscoelastic damping material that provides damping, which reduces the likelihood of resonance during operation of the motor. Such a viscoelastic material can also provide the required resilience/flexibility to provide the preload. An example of such a material is a Thermo Plastic Urethane like Dynaplast by GLS Corporation. Other materials resilient and/or flexible materials mentioned above for the bearing mount 260 could be adapted to provide the required damping by adding mica. A lightweight impeller also allows faster speed response of the impeller to changing conditions. Any unwanted fluctuations in pressure due the lack of shroud can be compensated for by quickly changing the impeller speed to return pressure to the desired level. The bearing mounts also provide vibration isolation.

Figure 28:
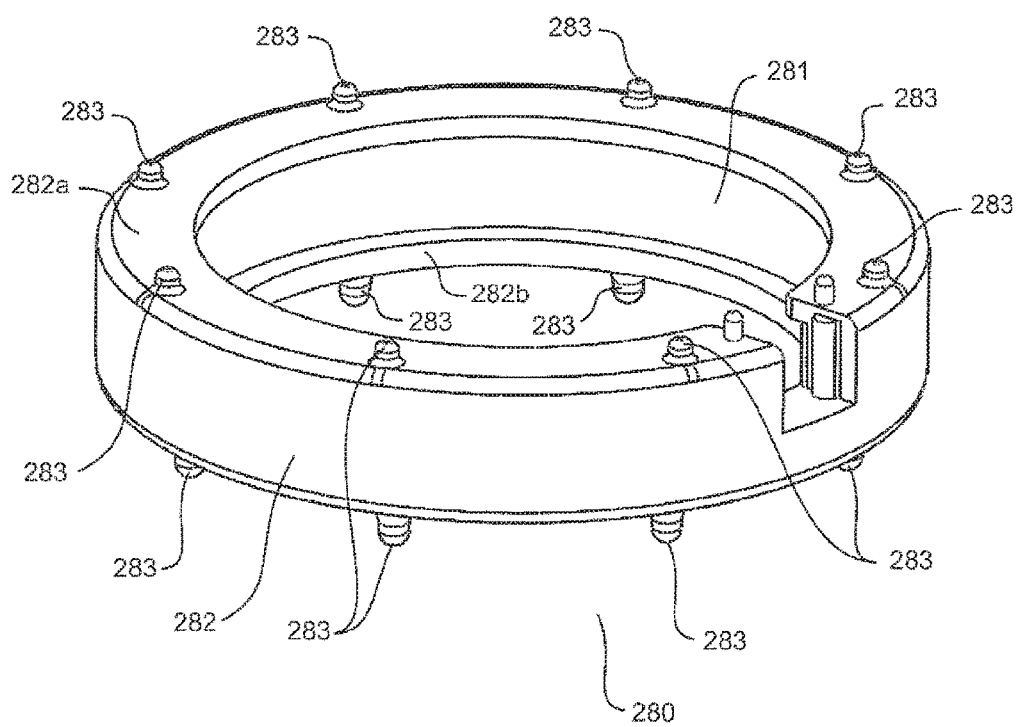
FIG. 28 shows a motor mounting structure of the second embodiment.

To provide further vibration damping of the rotational components of the blower, the motor and impeller, can optionally be mounted on a compliant mounting device (motor mount) 280. FIGS. 23, 27 and 28 shows one embodiment of such a mounting device 280. In accordance with the preferred embodiment of the invention the mount is most preferably made from a soft, flexible yet resilient material such as silicone rubber. The mounting device 280 has an annular body 282 with upper and lower engaging lips 282a, 282b that define an internal recess 281 in which the stator 241 is disposed. Preferably the internal recess 281 is smaller than the outer surface of the stator to encourage an interference fit between these components. FIG. 27 shows the motor positioned within the mounting recess 281.

A plurality of projections 283 encircles the upper and lower surfaces of the mount 280. The end of projection extends past the upper and lower surfaces of the mount to provide supporting leverage to the mount and motor assembly. During operation of the motor, vibration caused by any imbalance of the rotational components is absorbed by each of the projections by allowing the body of the mount 280 to move relative to the surface on which the projections 283 are supported.

The description above describes embodiments of a blower comprising a lightweight impeller assembly. FIGS. 19 and 27 show embodiments with a metal (e.g. steel) shaft 60 assembled on a magnet rotor 62. The metal shaft is press fit into an aperture in the magnet rotor. This requires fine tolerance control to ensure a good tight fit to reduce slipping. However, the fit should not be so tight as to risk cracking the magnet rotor.

Alternative shaft and magnet rotor assemblies are shown in FIGS. 30 to 33B, which can be used in the stator in place of the assembly shown in FIG. 19 or 27.

Figure 30A:
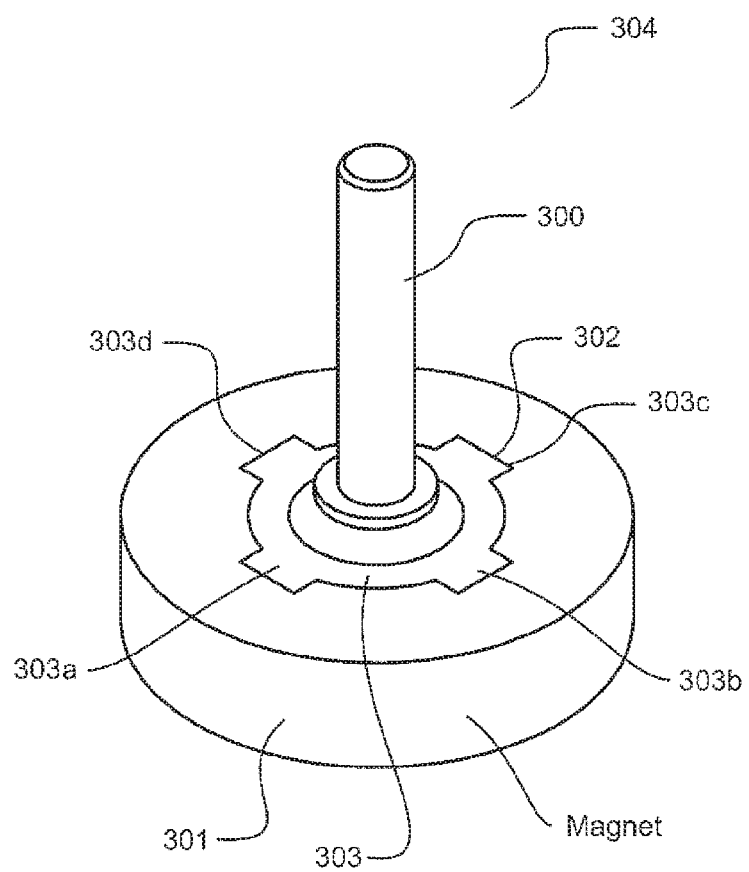
Figure 31:
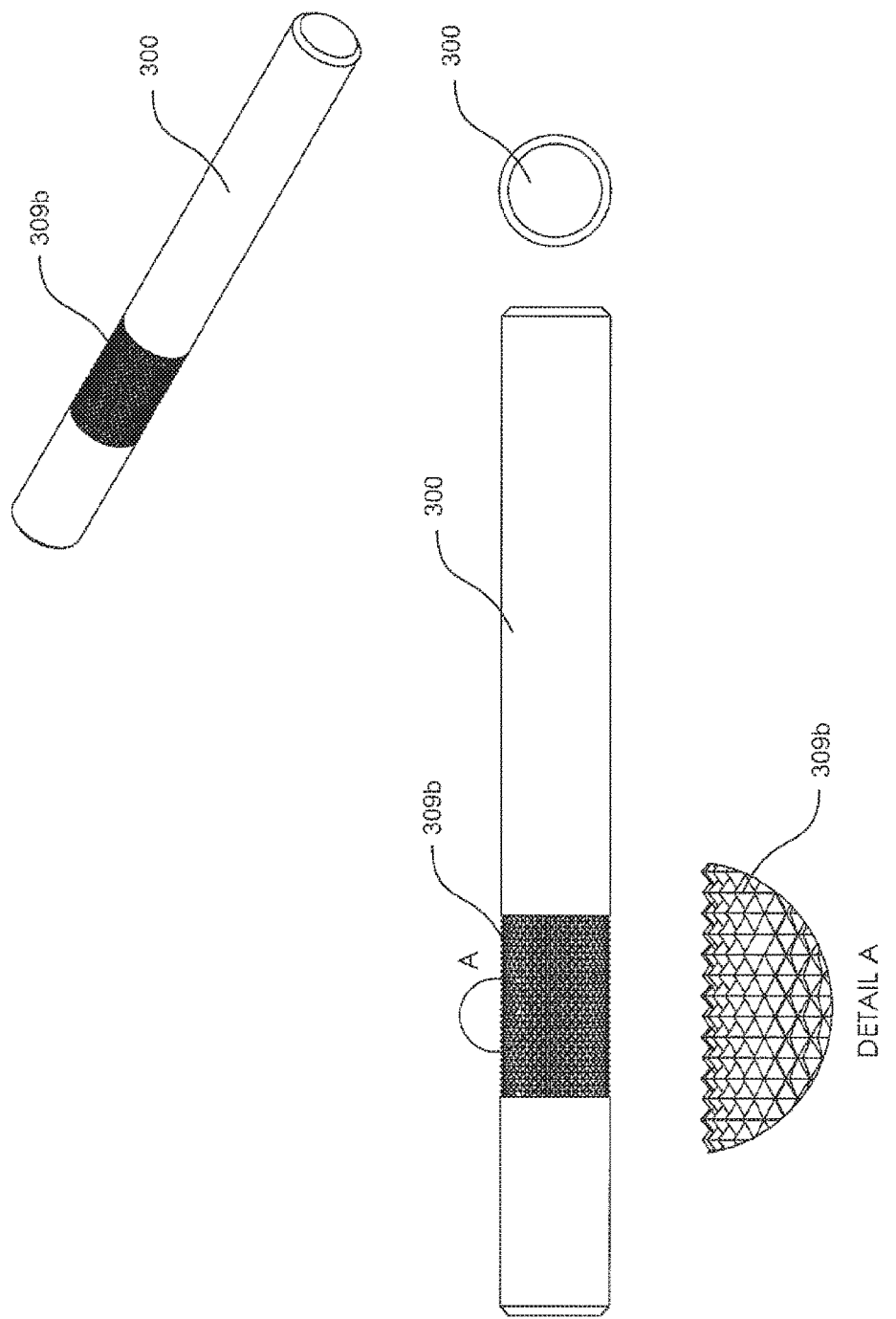
FIG. 31 shows the metal shaft of the assembly in FIGS. 30A, 30B.
Figure 34:
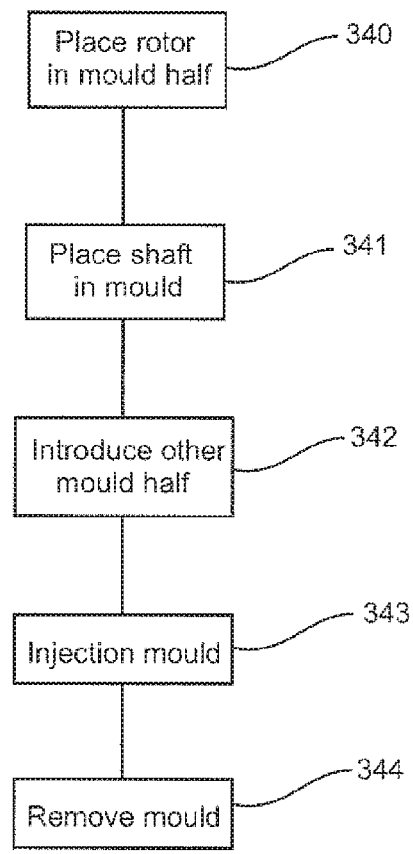
FIG. 34 shows a flow diagram of an injection moulding process for the metal shaft/insert rotor assembly.

FIGS. 30A, 30B and 31 show a possible alternative rotor assembly of the embodiments described above. The assembly comprises a metal shaft 300 (see FIG. 31) and a magnet rotor 301. The magnet rotor 301 has a central opening 302. The central opening 302 comprises a central portion with indents 303a to 303d. The central opening also comprises a profiled edge through a central cross-section providing a stepped ledge 308 (see FIG. 30B). The metal shaft 300 has a knurled section 309b in its exterior and extends through the central opening 302. A plastic insert 303 is injection moulded between the shaft 300 and the magnet rotor 301 in the central opening 302. The plastic insert 303 is overmoulded onto the stepped ledge 308 of the magnet rotor. This provides an insert 303 with a similar exterior shape to the central opening 302. An interlocking (cog dog) is formed between the shaft 300 and overmoulded (insert) material 303, so that the metal shaft knurled section 309b engages with the overmoulded insert 303 to couple the shaft 300 to the magnet rotor 301. The assembly 304 can be used in the embodiments described above such as an FIGS. 19 and 27, wherein the shaft 60 and magnet rotor 62 of those embodiments are replaced with the metal shaft 300/plastic insert 303/magnet rotor 301 assembly 304 as described in FIGS. 30A, 30B and 31. The assembly can be created as shown in FIG. 34. The rotor is placed in a mould, step 340, the shaft is introduced, step 341, the other mould half is introduced, step 342, the insert is injection moulded between the shaft/rotor, step 343, and then the mould removed, step 344.

Figure 32:
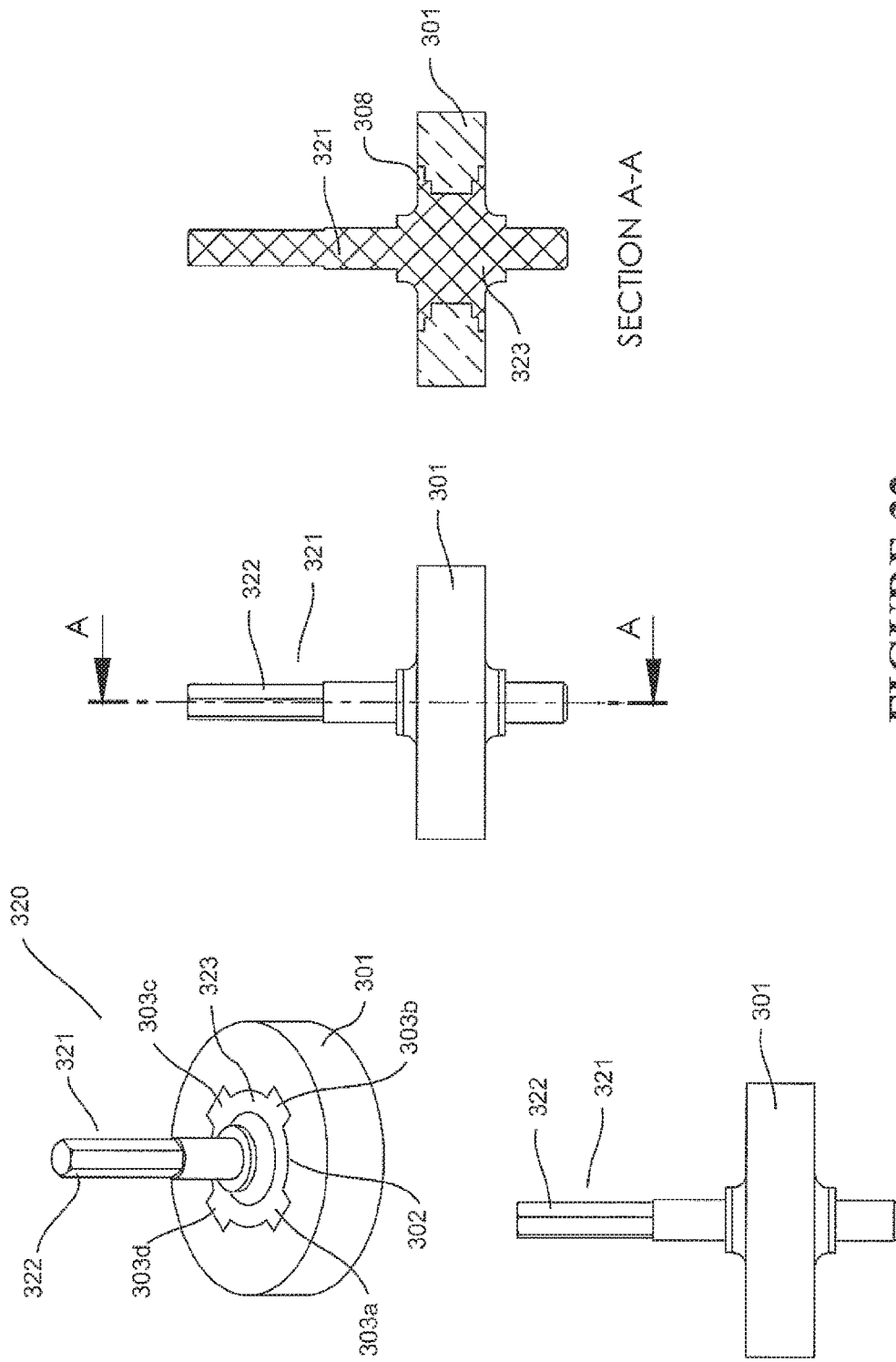
FIG. 32 shows a plastic shaft and magnet rotor assembly forming part of another embodiment of the motor.

FIG. 32 shows plan, elevation and isometric views of a magnet rotor and shaft assembly 320 according to another alternative embodiment. The assembly 320 comprises a rotor 301 formed from a magnet material. The magnet rotor 301 has a central opening 302. The central opening 302 comprises a central portion with indents 303a to 303d. The central opening also comprises a profiled edge through a central cross-section providing a stepped ledge 308.

The assembly 320 also comprises a plastic shaft 321 that extends through the centre of the insert opening 310 and is overmoulded onto the magnet rotor 301 as will described below. When overmoulded, the shaft comprises an integral overmould magnet insert portion 323. The shaft 321 can be formed to comprise a hex 322 or other location profile for press fit coupling with the impeller 24. The plastic shaft 321 comprises any suitable plastic or combination thereof, such as acety or polypropylene, although any suitable injection moulding or other plastic could be used.

The assembly 320 can be used in the embodiments described above such as an FIGS. 19 and 27, wherein the shaft 60 and magnet rotor 62 of those embodiments are replaced with the plastic shaft 321/magnet rotor 301 assembly 320 as described in FIG. 32.

Figure 33A:
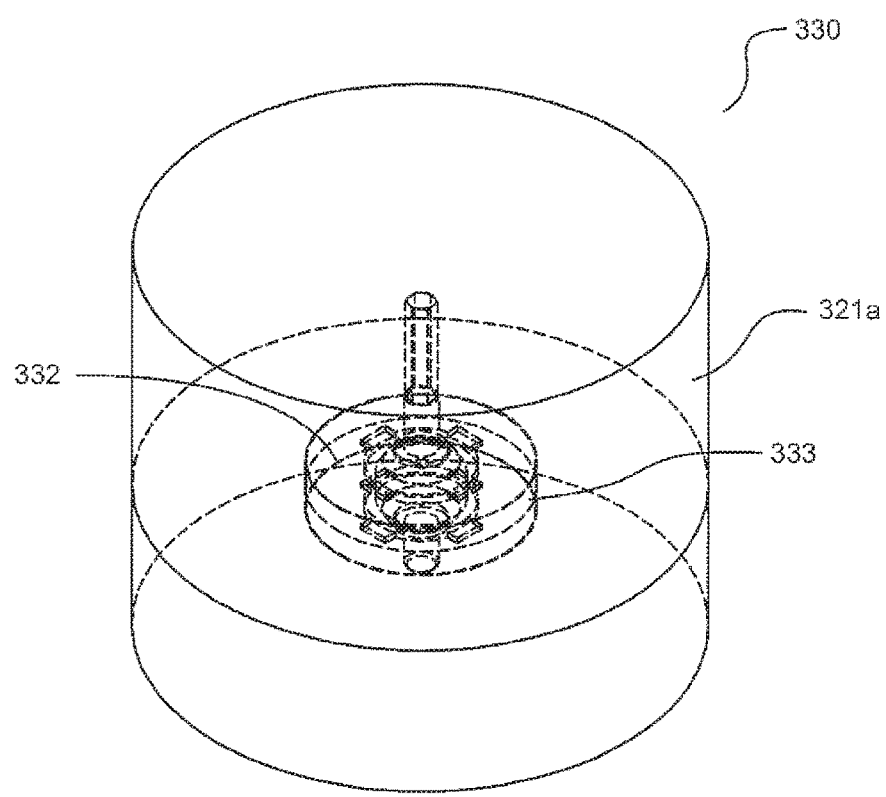
FIGS. 33A and 33B show an injection moulding tool for manufacturing the plastic shaft and rotor assembly of FIG. 32.
Figure 33B:
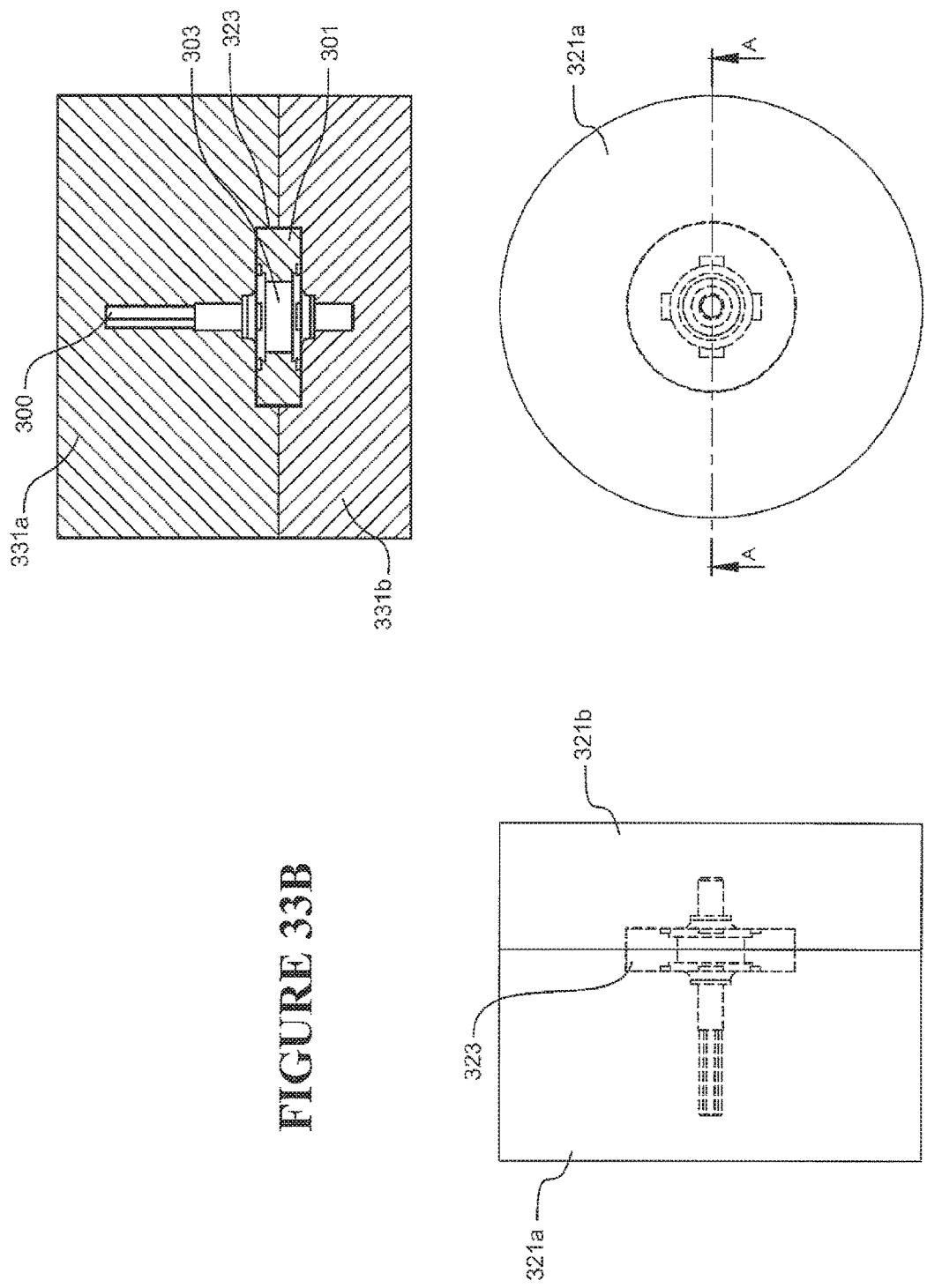
Figure 35:
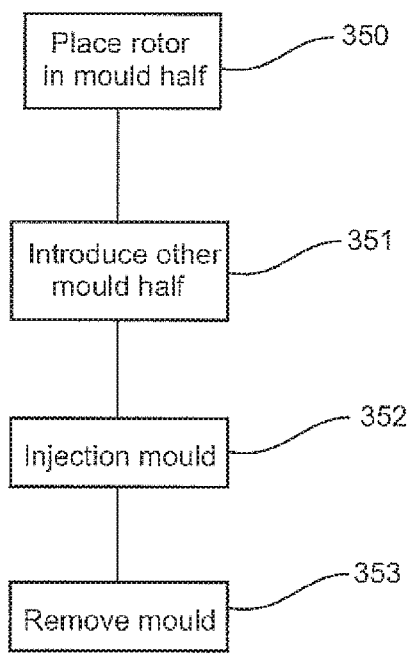
FIG. 35 shows a flow diagram of an injection moulding process for the plastic shaft rotor assembly.

FIGS. 33A and 33B show an injection moulding tool that can be used to manufacture the shaft/rotor assembly 320, and FIG. 35 is a flow diagram of a method of manufacture. The tool 330 is an open and close two-part mould tool comprising a first mould part/portion 331a and a second mould part/portion 331b that come together to form a mould/cavity 332 comprising a magnet jig 333. The mould comprises a cavity to form the shaft 321, hex fit shape 322 and overmould portion 323. During manufacture of the assembly 320, a magnet rotor 301 with an opening 302 as described above is introduced into the mould and placed in position in one half of the mould forming the jig 333, step 350. The top portion 321a of the mould is placed in position to create the mould cavity 332 with the bottom portion 321b, step 351. An injection moulding process starts, step 352, to injection mould plastic to create the shaft 321 overmoulded onto the magnet rotor 301. The injection moulding process overmoulds plastic over the stepped ledge 308 portion of the rotor magnet 301 to create the insert portion 323. Once the injection moulding process is complete, the mould portions 321a, 321b are removed leaving the assembly 320, step 353. The assembly 320 can then be used in the motor of FIG. 19 or FIG. 27, for example.

Previously, it has not been possible to use a plastic shaft/rotor assembly in the motor of a blower of a CPAP machine or similar. A plastic shaft is not sufficiently strong to withstand the forces involved in such motors. However, in the lightweight impeller embodiments described above, the forces are such that a plastic shaft rotor becomes a possibility. The lightweight and low inertia nature of the rotor along with the compliant bearing mount and other features that reduce unbalancing forces and other forces enable the use of a plastic shaft. Both the plastic rotor assembly and the method of manufacture provide advantages over existing metal shaft rotors.

The combination of various features of the present invention provide advantages, which can be achieved using a single impeller. Using a lightweight/low inertia impeller (e.g. by removing some or all of the shroud and/or reducing blade material) reduces imbalance of the impeller due to manufacturing tolerances. Previously, after manufacture and during assembly of a blower, it has been necessary to remove/add material to the impeller to improve balancing. The lightweight nature of the impeller means that any small imbalance can be tolerated without requiring rectification. Coupled to this, where the imbalance is not small enough, the resilient/flexible bearing structure mounts 65 and/or stator mount can compensate for any imbalance in the impeller. As the impeller is lightweight enough, any imbalance is of a small enough magnitude to be compensated for by the bearing structure mounts 65, without the need for altering the weight of the impeller during assembly.

The lightweight construction also allows for a larger diameter impeller, which in turn provides higher tip speed for a particular RPM. This allows for lower RPM operation of the blower while still achieving the required pressure (which is dependent on tip speed). Having a lower RPM reduces vibration to an acceptable level, or to a level that can be compensated for by the bearing structure and/or stator mount. The lightweight construction of the impeller as mentioned previously enables the larger impeller as it provides lower inertia that achieves the required pressures/response. That is, lower torque is required to speed up and slow down the impeller to reach the required tip speeds/pressures. This improves dynamic performance (response). In addition to this, small magnets in the motor (combined with the bearing structure) remove the need for balancing during assembly, improve dynamic performance.

The resilient/flexible bearing structure allows for self-alignment, compliance, damping and preload of the impeller and shaft assembly. This makes assembly easier, and in combination with the lightweight/low inertia impeller reduce or negates the need for balancing modifications during assembly, as mentioned previously. The bearing structure provides for relaxed tolerances during manufacture as it compensates for larger tolerances. The bearing structure also isolates and/or damps vibrations, also allowing high RPM speeds of the impeller where necessary. The stator frame/motor mount also provides vibration isolation.

The partition that separates the blower into first and second regions separates out the high velocity region to reduce noise. This allows for and maintains a constant high velocity of flow while diffusing the velocity to pressure.

The use of a plastic shaft also provides a number of benefits over a metal (e.g. steel) shaft, including (but not limited to) the following The reliability risks associated with dissimilar materials are reduced.

The knurled interface between the cog/dog insert and the shaft does not have to be monitored for cracking, slipping, run out, shrinkage, fluid ingress/corrosion.

The impeller to shaft interface is improved and carries similar reduced reliability risks. It is less prone to cracking because of similar thermal expansion (due to plastic on plastic press fitting). There is reduced chance of slipping because of the opportunity to add some keying feature like a hex or grooves.

The plastic shaft assembly is a press fit rather than a sliding fit so is more stable with less chance of rattles.

The cost relative to a metal shaft is reduced. This is because of the following.

Manufacturing the shaft to the tolerance for a sliding fit is not required because the plasticity of the plastic shaft allows for much wider tolerance or inaccuracy to press fit the bearings.

The need for grinding of the shaft after knurling to re-establish straightness is not required.

The handling and inserting the shaft into the mould is not required.

It is possible to use materials with better vibration absorption properties than steel.

Ease of assembly can be improved by reducing the length of the bearing press fit engagement by reducing shaft diameter with a hex, undercutting the impeller side of the shaft.

In general, the following advantages are provided for by the combination of one or more features as follows:

| Advantage | Features providing advantage |
| --- | --- |
| Low noise impeller | Low RPM (due to large diameter impeller) |
| | Partition to provide two regions, one containing the impeller |
| | Low cogging torque |
| | Sensorless vector drive/field oriented control |
| Fast responding blower | Low inertia impeller (achieved through shroudless/lightweight construction) |
| | Small magnet with diameter less than 20 mm |
| | Sensorless vector drive |
| Lower cost | No balancing required during assembly |
| | Small volume magnet |
| | Simple bearing mount |
| | One piece impeller |

-continued

| Advantage | Features providing advantage |
|---|---|
| Assembly without balancing | Low inertia impeller/lightweight<br>Flexible/resilient bearing structure<br>Motor mount/stator frame isolator<br>Low RPM impeller<br>Small magnet with diameter less than 20 mm<br>One piece impeller |
| Large diameter impeller/<br>Low RPM | Low inertia impeller |
| Simplified manufacture, lower costs, better reliability | Use of plastic shaft which becomes possible due to lightweight impeller, balancing advantages and other features |

Although the present invention has been described in terms of a certain embodiment, other embodiments apparent to those of ordinary skill in the art also are within the scope of this invention. Thus, various changes and modifications may be made without departing from the spirit and scope of the invention. For instance, various components may be repositioned as desired. Moreover, not all of the features, aspects and advantages are necessarily required to practice the present invention. Accordingly, the scope of the present invention is intended to be defined only by the claims that follow.

The invention claimed is:

1. A breathing assistance apparatus comprising:
a pressurised gases source comprising:
   a housing,
   a gases inlet,
   a gases outlet adapted to emit pressurised gases to an outlet of the breathing assistance apparatus,
a motor comprising:
   a rotor including a central opening including a ledge,
   a homogeneous rotatable plastic shaft contacting the ledge, thereby coupling the rotatable plastic shaft to the rotor,
   at least one bearing structure to support the rotatable plastic shaft within a stator, the at least one bearing structure having one or more flexible and/or resilient bearing mounts to provide compliance and/or preload and/or damping for the rotatable plastic shaft, and
   a lightweight impeller coupled to the rotatable plastic shaft.

2. The breathing assistance apparatus according to claim 1, further comprising a flexible and/or resilient motor mount that couples the stator and the housing to provide compliance and/or damping for the motor.

3. The breathing assistance apparatus according to claim 1, wherein the ledge spans a perimeter of the central opening.

4. The breathing assistance apparatus according to claim 1, wherein the rotatable plastic shaft engages with the ledge to prevent relative motion between the rotor and the rotatable plastic shaft.

5. The breathing assistance apparatus according to claim 1, wherein the central opening includes at least one indent projecting outwardly from the center of the central opening into the rotor.

6. The breathing assistance apparatus according to claim 1, wherein the rotor is formed from a magnet material.

7. The breathing assistance apparatus according to claim 1, wherein the central opening comprises a central portion with at least one indent.

8. The breathing assistance apparatus according to claim 1, wherein the central opening comprises a central portion with four indents.

9. The breathing assistance apparatus according to claim 1, wherein the central opening comprises a central portion with at least two equally spaced indents.

10. The breathing assistance apparatus according to claim 1, wherein the central opening comprises a profiled edge through a central cross-section providing the ledge.

11. The breathing assistance apparatus according to claim 1, wherein the ledge is a stepped ledge.

12. The breathing assistance apparatus according to claim 1, wherein the opening comprises three different diameters.

13. The breathing assistance apparatus according to claim 1, wherein the plastic shaft is overmoulded onto the rotor.

14. The breathing assistance apparatus according to claim 1, wherein the plastic shaft comprise a location profile for coupling with the lightweight impeller.

15. The breathing assistance apparatus according to claim 1, wherein the plastic shaft comprise a hex for coupling with the lightweight impeller.

16. The breathing assistance apparatus according to claim 1, wherein the plastic shaft comprises acety or polypropylene.

17. The breathing assistance apparatus according to claim 1, wherein the impeller is a shroudless impeller.

18. The breathing assistance apparatus according to claim 1, wherein the impeller has a mass less than two grams.

19. The breathing assistance apparatus according to claim 1, wherein the bearing mounts comprise an elastomeric material.

20. The breathing assistance apparatus according to claim 1, wherein the ledge is a first ledge, further comprising a second ledge on an opposite side of the rotor as the first ledge.

* * * * *

UNITED STATES PATENT AND TRADEMARK OFFICE
CERTIFICATE OF CORRECTION

PATENT NO. : 10,471,225 B2
APPLICATION NO. : 14/652687
DATED : November 12, 2019
INVENTOR(S) : Johannes Nicolaas Bothma et al.

Page 1 of 1

It is certified that error appears in the above-identified patent and that said Letters Patent is hereby corrected as shown below:

In the Specification

Column 2, Line 44, delete "apparatus"" and insert --apparatus".--.

Column 7, Line 20, delete "art" and insert --art.--.

Column 16, Line 20, delete "Flouro" and insert --Fluoro--.

Column 18, Lines 6-7, delete "magentisation" and insert --magnetization--.

Column 20, Line 59, delete "acety" and insert --acetyl--.

In the Claims

Column 24, Line 38, Claim 16, delete "acety" and insert --acetyl--.

Signed and Sealed this
Nineteenth Day of May, 2020

Andrei Iancu
*Director of the United States Patent and Trademark Office*